United States Patent [19]
Ozkaynak et al.

[11] Patent Number: 6,071,695
[45] Date of Patent: Jun. 6, 2000

[54] METHODS AND PRODUCTS FOR IDENTIFICATION OF MODULATORS OF OSTEOGENIC PROTEIN-1 GENE EXPRESSION

[75] Inventors: Engin Ozkaynak, Milford; Hermann Oppermann, Medway, both of Mass.

[73] Assignee: Creative Biomolecules, Inc., Hopkinton, Mass.

[21] Appl. No.: 08/486,343

[22] Filed: Jun. 7, 1995

Related U.S. Application Data

[63] Continuation-in-part of application No. 08/255,250, Jun. 7, 1994, abandoned, application No. 08/449,699, May 24, 1995, and application No. 08/449,700, May 23, 1995, Pat. No. 5,863,758, which is a division of application No. 08/147,023, Nov. 1, 1993, Pat. No. 5,468,845, which is a division of application No. 07/841,646, Feb. 21, 1992, Pat. No. 5,266,683, said application No. 08/449,699, is a continuation of application No. 08/147,023.

[51] Int. Cl.[7] .............................. C12Q 1/68; C12Q 1/02; C12N 5/10; C12N 15/85
[52] U.S. Cl. ............................. 435/6; 435/29; 435/320.1; 435/325; 536/23.1; 536/24.1
[58] Field of Search .................................. 435/320.1, 4.6, 435/29, 240.2, 325; 536/24.1, 23.1

[56] References Cited

U.S. PATENT DOCUMENTS

| | | | |
|---|---|---|---|
| 5,141,905 | 8/1992 | Rosen et al. | 435/69.1 |
| 5,266,683 | 11/1993 | Oppermann et al. | 530/326 |

FOREIGN PATENT DOCUMENTS

| | | |
|---|---|---|
| WO 91/01379 | 2/1991 | WIPO . |
| WO 92/21365 | 12/1992 | WIPO . |
| WO 93/05172 | 3/1993 | WIPO . |
| WO 93/20218 | 10/1993 | WIPO . |
| WO 94/28150 | 12/1994 | WIPO . |
| WO 95/11983 | 5/1995 | WIPO . |
| WO 95/14104 | 5/1995 | WIPO . |

OTHER PUBLICATIONS

Özkaynak et al. "OP–1 cDNA encodes an osteogenic protein in the TGF–beta family", EMBO J 9(7): 2085–2093, 1990.
M. Ponglikitmongkol et al., "Synergistic Activation of Transcription by the Human Estrogen Receptor Bound To Tandem Responsive Elements", *The Embo J.*, 9 (No. 7): 2225–2224 (Jul. 1990).
Rauscher III et al., "Binding of the Wilms' Tumor Locus Zinc Finger Protein to the EGR–1 Consensus Sequence", *Science*, 250 (No. 4985):1259–1262 (Nov. 30, 1990).
Mader et al., "A Steroid–Inducible Promoter For The Controlled Overexpression Of Cloned Genes In Eukaryotic Cells", *Proc. Natl. Acad. Sci. USA*, 90:5603–5607 (Jun. 1993).
Wang et al., "A Second Transcriptionally Active DNA–Binding Site For The Wilms Tumor Gene Product, WT1", *Proc. Natl. Acad. Sci. USA*, 90:8896–8900 (Oct. 1993).
Kuberasampath et al., EMBL Sequence—Dtabase, (1994), Acc. No. Q53142.
Zhou et al., "Wilms' tumor (WT1) gene expression in rat decidual differentiation", *Differentiation*, 54:109–114 (1993).
Sukhatme et al., "A Zinc Finger–Encoding Gene Coregulated with c–fos During Growth and Differentiation, and after Cellular Depolarization", *Cell*, 53:37–43, (1993).
Rupprecht et al., "The Wilms' Tumor Suppressor Gene WT1 Is Negatively Autoregulated", *The J. of Biological Chemistry*, 269:6198–6206 (1994).
Ray et al., "Down–modulation of Interleukin–6 Gene Expression by 17β–Extradiol in the Absence of High Affinity DNA Binding by the Extrogen Receptor", *The J. of Biological Chemistry*, 269:12940–12946 (1994).
Christy et al., "DNA binding site of the growth factor–inducible protein Zif268", *Proc. Natl. Acad. Sci. USA*, 86:8737–8741 (1989).
Zhao–Yi Wang et al., "An S1 Nuclease–sensitive Homopurine/Homopyrimidine Domain in the PDGF A–Chain Promoter Contains A Novel Binding Site For The Growth Factor–Inducible Protein EGR–1", Biochemical and Biophysical Research Communications, 188:433–439 (1992).
Zhao–Yi Wang et al., "A Second Transcriptionally active DNA–binding site for the Wilms Tumor gene product, WT1", Medical Sciences, 90:8896–8900 (1993).
Call et al., "Isolation and Characterization of a Zinc Finger Polypetide Gene at the Human Chromosome 11 Wilms' Tumor Locus", Cell, 60:509–520 (1990).
Gessler et al., "Homozygous deletion in Wilms tumours of a zinc–finger gene identified by chromosome jumping", Nature, 343:774–778 (1990).
Christy et al., "A gene activatied in mouse 3T3 cells by serum growth factors encodes a protein with "zinc finger" sequence", Biochemistry, 85:7857–7861 (1988).
Drummond et al., "Repression of the Insulin–Like Growth Factor II Gene by the Wilms Tumor Suppressor WT1", Science, 257:674–678.
Gashler et al., "Human platelet–derived growth factor A chain is transcriptionally repressed by the Wilms tumor suppressor WT1", Proc. Ntal, Acad. Sci. USA 89:10984–10988 (1992).
Klausner et al., "Cis–Trans Models for Post–Transcriptional Gene Regulation", Science 246:870–872 (1989).
Standart et al., "Maternal mRNA from clam oocytes can be specifically unmasked in vitro by antisense RNA complementary to the 3'–untranslated region", Genes & Development, 4:22157–2168 (1990).
Parker "Steroid and related receptors", Current Opinion in Cell Biology, S:499–504 (1993).

(List continued on next page.)

*Primary Examiner*—Scott D. Priebe
*Attorney, Agent, or Firm*—Testa, Hurwitz & Thibeault, LLP

[57] ABSTRACT

Disclosed are methods and compositions for screening compounds for their ability to modulate expression of a tissue morphogenetic protein, particularly OP-1, OP-1 homologs and closely related proteins, using one or more OP-1-specific, noncoding nucleotide sequences and a suitable reporter gene.

44 Claims, 4 Drawing Sheets

OTHER PUBLICATIONS

Wozney et al., "Growth factors influencing bone development", J. Cell Sci. Suppl. 13:149–156 (1990).

Rosen et al., "In Vivo and In Vitro Roles Of BMP Sleletal Formation and and Repair", J. of Cellular Biochemistry, Supplement 14E, Abstracts 14E, 0 004:33. (1990).

Celeste et al., "Highly Purified Bovine–Inductive Activity Contains Multiple Protein Species Related to BMP–2", *J. of Cellular Biochemistry,* Supplement 14E, Abstracts, 0105:54 (1990).

D'Alessandro et al., "Purification, Characterization and Activity of Recombinant Human BMP–5", J. of Cellular Biochemistry, Supplment 15F, Q 105:166 (1991).

Wozney "Bone Morphogenetic Proteins", Progress in Growth Factor Research 1:267–280 (1989).

Celeste et al., "Identification of Transforming growth factor $\beta$ family members present in bone–inductive purified from bovine bone", Proc. Natl. Acad. Sci. USA, 87:9843–9847 (1990).

Hahn et al., "A Bone Morphogenetic Protein Subfamily: Chromosomal Localization of Human Genes for BMP5, BMP6, and BMP7", Genomics, 14: 759–762 (1992).

Wozney "The Bone Morphogenetic Protein Family and Osteogenesis", Molecular Reproduction and Development, 32:160–167 (1992).

Kreidberg et al., "WT–1 is Required for Early Kidney Development" Cell, 74:679–691 (1993).

Fig. 1B

METHODS AND PRODUCTS FOR IDENTIFICATION OF MODULATORS OF OSTEOGENIC PROTEIN-1 GENE EXPRESSION

REFERENCE TO RELATED APPLICATIONS

This application is a continuation-in-part of (1) U.S. Ser. No. 08/255,250, filed Jun. 7, 1994, now abandoned; (2) U.S. Ser. No. 08/449,699, filed May 24, 1995, which is a continuation of U.S. Ser. No. 08/147,023, filed Nov. 1, 1993 (U.S. Pat. No. 5,468,845), and (3) U.S. Ser. No. 08/449,700, filed May 23, 1995, (U.S. Pat. No. 5,863,758) which is a divisional of U.S. Ser. No. 08/147,023, filed Nov. 1, 1993 (U.S. Pat. No. 5,468,845), which is a divisional of U.S. Ser. No. 07/841,646, filed Feb. 21, 1992 (U.S. Pat. No. 5,266,683), the disclosures of which are incorporated herein by reference.

FIELD OF THE INVENTION

The invention relates generally to the field of drug screening assays. More particularly, the invention relates to methods and compositions for identifying molecules that modulate production of true tissue morphogenic proteins.

BACKGROUND OF THE INVENTION

A class of proteins recently has been identified, the members of which are true tissue morphogenic proteins. The members of this class of proteins are characterized as competent for inducing the developmental cascade of cellular and molecular events that culminate in the formation of new organ-specific tissue, including any vascular and connective tissue formation as required by the naturally occurring tissue. Specifically, the morphogens are competent for inducing all of the following biological functions in a morphogenically permissive environment: (1) stimulating proliferation of progenitor cells; (2) stimulating differentiation of progenitor cells; (3) stimulating the proliferation of differentiated cells and (4) supporting the growth and maintenance of differentiated cells. For example, the morphogenic proteins can induce the full developmental cascade of bone tissue morphogenesis, including the migration and proliferation of mesenchymal cells, proliferation and differentiation of chondrocytes, cartilage matrix formation and calcification, vascular invasion, osteoblast proliferation, bone formation, bone remodeling, and hematopoietic bone marrow differentiation. These proteins also have been shown to induce true tissue morphogenesis of non-chondrogenic tissue, including dentin, liver, and nerve tissue.

A particularly useful tissue morphogenic protein is human OP-1 (Osteogenic Protein-1), described in U.S. Pat. No. 5,011,691; U.S. Pat. No. 5,266,683 and Ozkaynak et al. (1990) *EMBO J.* 9: 2085–2093. Species homologues identified to date include mouse OP-1 (see U.S. Pat. No. 5,266,683) and the Drosophila homologue 60A, described in Wharton et al. (1991) *PNAS* 88:9214–9218). Other closely related proteins include OP-2 (Ozkaynak (1992) *J. Biol. Chem.* 267:25220–25227 and U.S. Pat. No. 5,266,683); BMP5, BMP6 (Celeste et al. (1991) *PNAS* 87:9843–9847) and Vgr-1 (Lyons et al. (1989). These disclosures are incorporated herein by reference.

It previously has been contemplated that these tissue morphogens can be administered to an animal to regenerate lost or damaged tissue. Alternatively, one can envision administering a molecule capable of modulating expression of the endogenous tissue morphogen as a means for providing morphogen to a site in vivo.

It is an object of this invention to provide compositions and methods of screening compounds which can modulate expression of an endogenous tissue morphogen, particularly OP-1 and closely related genes. The compounds thus identified have utility both in vitro and in vivo. Useful compounds contemplated include those capable of stimulating transcription and/or translation of the OP-1 gene, as well as compounds capable of inhibiting transcription and/or translation of the OP-1 gene.

These and other objects and features of the invention will be apparent from the description, drawings and claims which follow.

SUMMARY OF THE INVENTION

The invention features compositions and methods for screening candidate compounds for the ability to modulate the effective local or systemic quantity of endogenous OP-1 in an organism, and methods for producing the compounds identified. In one aspect, the method is practiced by: (1) incubating one or more candidate compounds with cells transfected with a DNA sequence encoding, in operative association with reporter gene, a portion of an OP-1 non-coding DNA sequence that is competent to act on and affect expression of the associated receptor gene; (2) measuring the level of reporter gene expression in the transfected cell, and (3) comparing the level of reporter gene expressed in the presence of the candidate compound with the level of reporter gene expressed in the absence of the candidate compound. In a related aspect, the invention features the compound that is identified by use of the method of the invention.

The screening method of the invention provides a simple method of determining a change in the level of a reporter gene product expressed by a cell following exposure to one or more compound(s). The level of an expressed reporter gene product in a given cell culture, or a change in that level resulting from exposure to one or more compound(s) indicates that application of the compound can modulate the level of the morphogen expressed and normally associated with the non-coding sequence. Specifically, an increase in the level of reporter gene expression is indicative of a candidate compound's ability to increase OP-1 expression in vivo. Similarly, a decrease in the level of reporter gene expression is indicative of a candidate compound's ability to decrease or otherwise interfere with OP-1 expression in vivo.

The methods and compositions of the invention can be used to identify compounds showing promise as therapeutics for various in vivo and ex vivo mammalian applications, as well as to identify compounds having numerous utilities. For example, morphogen expression inducing compounds can be used in vivo to correct or alleviate a diseased condition, to regenerate lost or damaged tissue, to induce cell proliferation and differentiation, and/or to maintain cell and tissue viability and/or a differentiated phenotype in vivo or ex vivo. The compounds also can be used to maintain the viability of, and the differentiated phenotype of, cells in culture. The various in vivo, ex vivo, and in vitro utilities and applications of the morphogenic proteins described herein are well documented in the art. See, for example, US 92/01968 (WO 94/03200), filed Mar. 11, 1992; US 92/07358 (WO 93/04692), filed Aug. 28; PCT US 92/0743 (WO 93/05751), filed Aug. 28, 1992; US 93/07321 (WO 94/03200), filed Jul. 29, 1993; US 93/08808 (WO 94/06449), filed Sep. 16, 1993; US93/08885 (WO94/06420), filed Sep. 15, 1993, and U.S. Pat. No. 5,266,683.

Morphogen expression inhibiting compounds identified by the methods, kits and compositions described herein can be used to modulate the degree and/or timing of morphogen expression in a cell. Such compounds can be used both in vitro and in vivo to more closely regulate the production and/or available concentration of morphogen.

LIST OF USEFUL TERMS AND DEFINITIONS

As used herein, "gene expression" is understood to refer to the production of the protein product encoded by a DNA sequence of interest, including the transcription of the DNA sequence and translation of the mRNA transcript.

As used herein, "operative association" is a fusion of the described DNA sequences with a reporter gene in such at reading frame as to be co-transcribed, or at such a relative positioning as to be competent to modulate expression of the reporter gene.

As used herein, "vector" is understood to mean any nucleic acid comprising a nucleotide sequence of interest and competent to be incorporated into a host cell and recombining with and integrating into the host cell genome. Such vectors include linear nucleic acids, plasmids, phagemids, cosmids, YAC'S (yeast artificial chromosomes) and the like.

As used herein, "non-coding sequence" or "non-coding DNA" includes DNA sequences that are not transcribed into RNA sequence, and/or RNA sequences that are not translated into protein. This category of "non-coding sequence" has been defined for ease of reference in the application, and includes sequences occurring 5' to the ATG site which indicates the start codon and sequences 3' to the stop codon, as well as intervening intron sequences that occur within the coding region of the gene. As used herein, an "OP1-specific" non-coding sequence is understood to define a non-coding sequence that lies contiguous to OP1 specific coding sequence at an OP-1 gene locus under naturally-occurring conditions. The sequences may include 5', 3' and intron sequences.

As used herein, "allelic, species and other sequence variants thereof" includes point mutations, insertions and deletions such as would be naturally occurring or which can genetically engineered into an OP-1 non-coding DNA sequence and which do not affect substantially the regulation of a reporter gene by the OP-1 non-coding sequence. For example, one of ordinary skill in the art can use site directed mutagenesis to modify, as by deletion, for example, one or more of the OP-1 non-coding sequences described herein without substantially affecting the regulation of OP-1 or a reporter gene by the modification. Such modifications are considered to be within the scope of the disclosure provided herein.

As used herein, a "Wt-1/Egr-1 consensus binding sequence" or Wt-1/Egr-1 consensus binding element" is a nine base sequence which has been shown to be bound by the DNA binding proteins Wt-1 and Egr-1. The consensus sequence of the Wt-1/Egr-1 binding site has been determined by homology to be GNGNGGGNG, Seq. ID No. 4 (Rauscher et al., *Science* 250:1259–1262 (1990), incorporated herein by reference).

As used herein, a "TCC binding sequence" or "TCC binding element" is an approximately 15 to 20 base sequence of DNA which contains at least three contiguous or non-contiguous repeats of the DNA sequence TCC. The TCC binding sequence identified in human OP-1 genomic DNA is shown in Seq. ID No. 5, and the TCC binding sequence identified in murine OP-1 genomic DNA is shown in Seq. ID No. 6. The TCC binding sequence has also been shown to be bound by the DNA binding proteins Wt-1 and Egr-1 (Wang et al., *Proc. Natl. Acad. Sci.* 90:8896–8900 (1993); Wang et al., *Biochem Biophys Res. Comm.*, 188:433–439 (1992)).

As used herein, a "FTZ binding sequence" or "FTZ binding element" is a Fushi-tarazu DNA sequence (FTZ) that has been shown to be bound by the DNA binding protein Fushi-tarazu (FTZ-F1). The FTZ binding sequence identified in human OP-1 genomic DNA is shown in Seq. ID No. 7. The FTZ consensus sequence, a consensus sequence for the nuclear hormone receptor superfamily, is YCAAG-GYCR.

As used herein, a "steroid binding sequence" or "steroid binding element" i.e., steroid responsive element, is a DNA sequence that has been shown to be bound by one or more elements, in response to activating signal molecules. Examples of such "activating signal molecules" include retinoids, Vitamin D, and also include steroids such a estrogen and progesterone. Useful elements are anticipated to include the FTZ-F1 protein, WT-1 and Egr-1. Activating signal molecules of the nuclear receptor family have recently been shown to bind to DNA as homodimers, heterodimers or as monomers (Parker, M. G., Curr. Op. Cell Biol., 1993, 5:499–504). The formation of heterodimers among the nuclear receptor family molecules may significantly increase the diversity of binding elements which are recognized by these nuclear receptors, and provide for differential regulation of genes containing the specific binding sites. In addition, the nuclear receptors have been shown to interact with other accessory factors, such as transcription factors, to stimulate or repress transcription. These interactions, between the nuclear receptors and the nuclear receptors and accessory factors, indicate that there could be significant number of nuclear receptor/accessory factor interactions which have widely different transcriptional activities.

While the method of the invention is described with reference to a single cell, as will be appreciated by those having ordinary skill in the art, this is only for ease of description, and the method is most efficiently carried out using a plurality of cells.

With respect to transfection of DNA sequences in the cell and the method of the invention, all means for introducing nucleic acids into a cell are contemplated including, without limitation, $CaPO_4$ co-precipitation, electroporation, DEAE-dextran mediated uptake, protoplast fusion, microinjection and lipofusion. A key to the invention is the DNA sequences with which the cell is transfected, rather than the mechanical or chemical process by which the DNA incorporation is accomplished.

Useful reporter genes are characterized as being easy to transfect into a suitable host cell, easy to detect using an established assay protocol, and genes whose expression can be tightly regulated. Other reporter genes contemplated to have utility include, without limitation, the luciferase gene, the Green Fluorescent Protein (GFP) gene, the chloramphenicol Acetyl Transferase gene (CAT), human growth hormone, and beta-galactosidase. Additional useful reporter genes are any well characterized genes the expression of which is readily assayed, and examples of such reporter genes can be found in, for example, F. A. Ausubel et al., Eds., *Current Protocols in Molecular Biology*, John Wiley & Sons, New York, (1989). As will be appreciated by those having ordinary skill in the art, the listed reporter genes are only a few of the possible reporter genes, and it is only for ease of description that all available reporter genes are not listed.

While the method, vectors, and cells described recite the use of a reporter gene in operative association with an OP-1 non-coding DNA sequence, it will be apparent to those of ordinary skill in the art that the DNA sequence OP-1, including human OP1, shown in Seq. ID No. 1 or murine OP-1, disclosed in U.S. Pat. No. 5,266,683, is also within the scope of a suitable reporter gene. Other suitable reporter genes can be used for ease in assaying for the presence of the reporter mRNA or reporter gene product.

Where a cell line is to be established, particularly where the transfected DNA is to be incorporated into the cell's genome, lines that can be immortalized are especially desirable. As used herein, "immortalized" cell lines are viable for multiple passages (e.g., greater than 50 generations) without significant reduction in growth rate or protein production.

While the selected non-coding DNA sequences disclosed herein are described using defined bases, as will be appreciated by those having ordinary skill in the art, to some degree the lengths of the selected DNA sequences recited are arbitrary and are defined for convenience. As will be understood by those of ordinary skill in the art, shorter sequences of OP-1 non-coding DNA sequence and other fusion DNA's can be used in a vector according to the invention, and can be transfected into a cell, or used in the method of the invention for screening a candidate compound for its ability to modulate OP-1 expression. Specifically, it is standard procedure for molecular biologists to first identify useful regulatory sequences, and then to determine the minimum sequence required, by systematic digestion and mutagenesis e.g., by exonuclease or endonuclease digestion, site directed mutagenesis and the like. Accordingly, subsequent, standard routine experimentation is anticipated to identify minimum sequences and these, shorter sequences are contemplated by the invention disclosed herein.

Useful cell types for the method and compositions according to the invention include any eukaryotic cell. Currently preferred are cell types known to express OP-1. Such cells include epithelial cells and cells of uro-genital cell origin, including renal (kidney or bladder) cells, as well as liver, borne, nerve, ovary, cardiac muscle and the like. The cells may be derived from tissue or cultured from an established cell line. See, for example ozkaynak et al. (1991) *Biochem. BioPhys. Res. Comm.* 179:116–123 for a detailed description of tissues known to express OP-1. Other useful cells include those known to exhibit a steroid receptor, including cells having an estrogen receptor and cells responsive to the FTZ-F1 protein. Currently preferred cells also have simple media component requirements. Other useful representative cells include, but are not limited to, Chinese hamster ovary (CHO); canine kidney (MDCK); or rat bladder (NBT-2), and the like. Useful cell types can be obtained from the American Type Culture Collection (ATCC), Rockville, Md. or from the European Collection of Animal Cell Cultures, Portion Down, Salisbury SP40JG, U.K. As used herein, "derived" means the cells are from the cultured tissue itself, or are a cell line whose parent cells are of the tissue itself.

ASPECTS AND EMBODIMENTS OF THE INVENTION

In one aspect, the invention features a vector having a reporter gene operatively associated with a portion of one or more OP-1 non-coding sequences. The OP-1 non-coding sequence chosen is independently selected from the 5' (or "upstream") non-coding human or murine OP-1 sequence shown in Seq. ID Nos. 1 and 2, respectively, the 3' (or "downstream") non-coding human or murine OP-1 sequence shown in Seq. ID Nos. 1 or 3, and the human intron non-coding OP-1 sequences shown in Seq. ID No. 1. Also anticipated to be useful are the non-coding sequences (e.g., 5', 3' and intron) of other species homologs of OP-1 and proteins closely related to OP-1. In addition, the portion of OP-1 sequence included in the vector can be a combination of two or more 5' non-coding, 3' non-coding and/or intron OP-1 sequences.

In one embodiment, the vector can include a non-coding OP1-specific sequence selected from at least one of the following sequence segments of Seq. ID No. 1 presented below, and which define human genomic OP-1 sequence comprising approximately 3.3 Kb of 5' non-coding sequence. In Seq. ID No. 1, the start codon begins at position 3318, and the upstream sequence (be.ses 1 to 3317) is composed of untranscribed (1 to 2790) and untranslated (2791 to 3317) OP1-specific DNA; approximately 1 Kb of which is presented in FIG. 1 (bottom strand).

Useful sequence segments include bases 2548–3317, representing 750 bases sharing significant (greater than 70% identity) between the mouse and human OP-1 homologs (See FIG. 1), and bases 3170–3317; 3020–3317; 2790–3317; 2548–2790 of Seq. ID No. 1, all shorter fragments of this region of the DNA. As base 2790 is the mRNA start site, other useful sequences include 2790–3317, representing transcribed but not translated 5' coding sequence and shorter fragments of this DNA region as noted above; upstream fragments of OP1-specific DNA, bases 2548–2790; 1549–2790; 1–2790 of Seq. ID No. 1. Also useful sequence segments include the approximately 750 bases that have homology between the human and mouse OP-1 sequences with additional upstream sequences, 2300 to 3317,; 1300 to 3317; 1–3317; all fragments of the disclosed upstream OP1-specific DNA sequences of Seq. ID No. 1.

In another embodiment, the sequences are defined by the non-coding sequences of the mouse OP-1 homolog, including the following 5' non-coding sequences (Seq. ID No. 2): 2150–2296, 2000–2296, 1788–2296, and 1549–2296 all of which define the 750 bases sharing high sequence identity with the human homolog (See, FIG. 1); 800–2296; 1–2296; 1549–1788, 800–1788 and 1–1788.

Within this region also exist a number Egr/Wt-1 sites (8 in hOP-1; 7 in mOP-1), known in the art to bind the regulatory elements Egr and Wt-1. Accordingly, in another aspect, the invention contemplates a screening material for identifying compounds which modulate OP-1 expression, the assay comprising the step of identifying compounds which bind Egr/Wt-1 site. At least one Wt/Egr-1 element, preferably between 1–6 elements, or at least 6 Wt/Egr-1 elements are included in a sequence. The relative locations of these elements are indicated in FIG. 1 and at positions 3192–3200; 3143–3151; 3027–3035; 2956–2964; 2732–2740; 2697–2704 of Seq. ID No. 1, and positions 2003–2011; 1913–1922; 1818–1826; 1765–1776; 1757–1765; 1731–1739; 1699–1707; 1417–1425 of Seq. ID No. 2 of Seq. ID Nos. 1, 2 substantially the same Seq. alignment. The lengths of bases within these 5' non-coding sequences is selected to include portions of the sequence of DNA which was determined to be homologous between murine and human genomic OP-1, separately and as a part of a larger sequence including non-homologous DNA. Additionally, the portion of OP-1 sequence selected can be a portion of the region of homology between murine and human OP-1 DNA sequences, bases 2548–2790 or 2548–3317 of Seq. ID No. 1, or bases 1549 to 1788 or 1549 to 2296 of Seq. ID No. 2, and/or at least one of an Wt-1/Egr-1 consensus binding sequence. In still another aspect the portion of OP-1 sequence selected can include a TCC binding sequence, a FTZ binding sequence, a steroid binding sequence, or part or all of an OP-1 intron sequence. The relative positions of the TCC and FTZ elements are indicated in FIG. 1 and at positions 2758–2778 (TCC); 2432–2441 (FTZ) of Seq. ID No. 1 and 1755–1769 (TCC) of Seq. ID No. 2.

In another aspect, the invention features a cell that has been transfected with a reporter gene in operative association with a portion of OP-1 non-coding DNA sequence. The portion of OP-1 non-coding sequence is independently selected from the 5' (or upstream) non-coding human or murine OP-1 sequence shown in Seq. ID Nos. 1 and 2, the 3' (or downstream) non-coding murine OP-1 sequence shown in Seq. ID No. 3, and the human intron non-coding OP-1 sequence shown in Seq. ID No. 1. The six human intron non-coding OP-1 sequences are at bases 3736 to 10700; bases 10897 to 11063; bases 11217 to 11424; bases 11623 to 13358; bases 13440 to 15048; bases 15166 to 17250; all of Seq. ID No. 1. In addition the portion of OP-1 sequence selected can be a combination of 5' non-coding, 3' non-coding and/or intron OP-1 sequence. Thus, the cell can have been transfected with a reporter gene in operative association with a portion of 5' non-coding OP-1 genomic sequence that is independently selected from bases 3170 to 3317; 3020 to 3317; 2790 to 3317; 2548 to 3317; 2300 to 3317; 1300 to 3317; 1 to 3317; 2548 to 2790; 1549 to 2790; and 1 to 2790; all of Seq. ID No. 1 or bases 2150 to 2296; 2000 to 2296; 1788 to 2296; 1549 to 2296; 800 to 2296; 1 to 2296; 1549 to 1788; 800 to 1788; 1 to 1788; all of Seq. ID No. 2. The lengths of bases within these 5' non-coding sequences is selected to include portions of the sequence of DNA which was determined to be homologous between murine and human genomic OP-1, separately and as a part of a larger sequence including non-homologous DNA. Additionally, the portion of OP-1 sequence selected can be a portion of the region of homology between murine and human OP-1 DNA sequences, such as bases 2548–2790 or 2548–3317 of Seq. ID No. 1, or bases 1549 to 1788 or 1549 to 2296 of Seq. ID No. 2, and at least ore of an Wt-1/Egr-1 consensus binding sequence, a TCC binding sequence, a FTZ binding sequence, a steroid binding sequence, and an intron. Thus the portion of OP-1 sequence selected can be a portion of the 5' non-coding human or murine OP-1 genomic DNA sequences, as stated above, and at least one Wt-1/Egr-1 consensus binding sequence alone or in combination with at least one of a TCC binding sequence, a FTZ binding sequence, a steroid binding sequence, and a human OP-1 intron DNA sequence. In another embodiment more than one Wt-1/Egr-1 element is used, for example, between 1–6, or at least six. These cells are suitable for use in the method of the invention.

In one embodiment, part of the OP-1 coding region is anticipated to have an expression regulatory function and also can be added to a vector for use in the screening assay described herein. OP-1 protein is translated as a precursor polypeptide having an N-terminal signal peptide sequence (the "pre pro" region) which is typically less than about 30 amino acid residues, followed by a "pro" region which is about 260 amino acid residues, followed by the additional amino acid residues which comprise the mature protein. The pre pro and pro regions are cleaved from the primary translation sequence to yield the mature protein sequence. The mature sequence comprises both a conserved C-terminal seven cysteine domain and an N-terminal sequence which varies significantly in sequence between the various morphogens. The mature polypeptide chains dimerize and these dimers typically are stabilized by at least one interchain disulfide bond linking the two polypeptide chain subunits. After the pro domain is cleaved from the OP-1 protein it associates noncovalently with the mature dimeric protein, presumably to enhance solubility and/or targeting properties of the mature species. See, for example, PCT/US93/07189, filed Jul. 29, 1993. The pro region represents the nucleotide sequence occurring approximately 87 bases downstream of the ATG start codon, and continues for about 980 bases. The nucleotide sequence encoding the pro region is highly enriched in a "GC" sequence, which well may be competent to form a secondary structure (e.g., as part of the mRNA transcript) which itself may modulate OP-1 expression. Accordingly, part or all of the nucleotide sequence encoding an OP-1 pro region, particularly that portion corresponding to a GC rich region, may be used, preferably in combination with one or more OP-1 non coding sequences, in the compositions and methods of the invention.

In another embodiment, the method can be practiced using a cell known to express the OP-1 gene. Suitable DNA sequences for transfection are described below, as well as suitable cells containing transfected DNA sequences.

In another aspect, the invention provides molecules, vectors, methods and kits useful in the design and/or identification of OP-1 expression modulating compounds. As used herein a "kit" comprises a cell transfected with a DNA sequence comprising a reporter gene in operative association with a portion of OP-1 upstream DNA sequence and the reagents necessary for detecting expression of the reporter gene. The portion of OP-1 upstream DNA chosen can be any of the various portions which have been described herein.

Following this disclosure, medium flux screen assays, and kits therefore, for identifying OP-1 expression modulating compounds are available. These compounds can be naturally occurring molecules, or they can be designed and biosynthetically created using a rational drug design and an established structure/function analysis methodology. The compounds can be amino acid-based or can be composed in part or whole of non-proteinaceous synthetic organic molecules.

The OP-1 expression modulating compounds thus identified then can be produced in reasonable quantities using standard recombinant expression or chemical synthesis technology well known and characterized in the art and/or as described herein. For example, automated means for the chemical synthesis of nucleic and amino acid sequences are commercially available. Alternatively, promising candidates can be modified using standard biological or chemical methodologies to, for example, enhance the binding affinity of the compound for a DNA element and the preferred candidate derivative then can be produced in quantity.

Once a candidate compound has been identified it can be tested for its effect on OP-1 expression. For example, a compound which upregulates (increases) the production of OP-1 in a kidney cell line is a candidate for systemic administration. The candidate can be assayed in an animal model to determine the candidate molecule's efficacy in vivo. For example, the ability of a compound to upregulate levels of circulating OP-1 in vivo can be used to correct bone metabolism diseases such as osteoporosis (See, for example, PCT/US92/07932, supra). Useful in vivo animal models for systemic administration are disclosed in the art and below.

As demonstrated herein below, OP-1 is differentially expressed in different cell types. Accordingly, it further is anticipated that a candidate compound will have utility as an inducer of OP-1 expression in one cell type but not in another. Thus, the invention further contemplates testing a candidate compound for its utility in modulating expression of OP-1 in different cells in vivo, including different cells known to express OP-1 under native physiological conditions.

Thus, in view of this disclosure, one of ordinary skill in recombinant DNA techniques can design and construct appropriate DNA vectors and transfect cells with appropriate DNA sequences for use in the method according to the invention to assay for compounds which modulate the expression of OP-1. These identified compounds can be used to modulate OP-1 production and its available concentrations in both in vivo and in vitro contexts.

BRIEF DESCRIPTION OF THE DRAWINGS

FIG. 3, Panel B shows a Northern blot hybridization analysis of OP-1 specific 2 kb and 4 kb mRNAs in murine uterine tissue. Lanes 1 through 7 correspond to probes 1 through 7 respectively. The 2 kb and 4 kb mRNAs are indicated by the 4- and 2-on the left side of FIG. 3b, and a 0.24 to 9.49 kb RNA size ladder is indicated by dashes to the right of the figure.

DETAILED DESCRIPTION

Figure 1A:
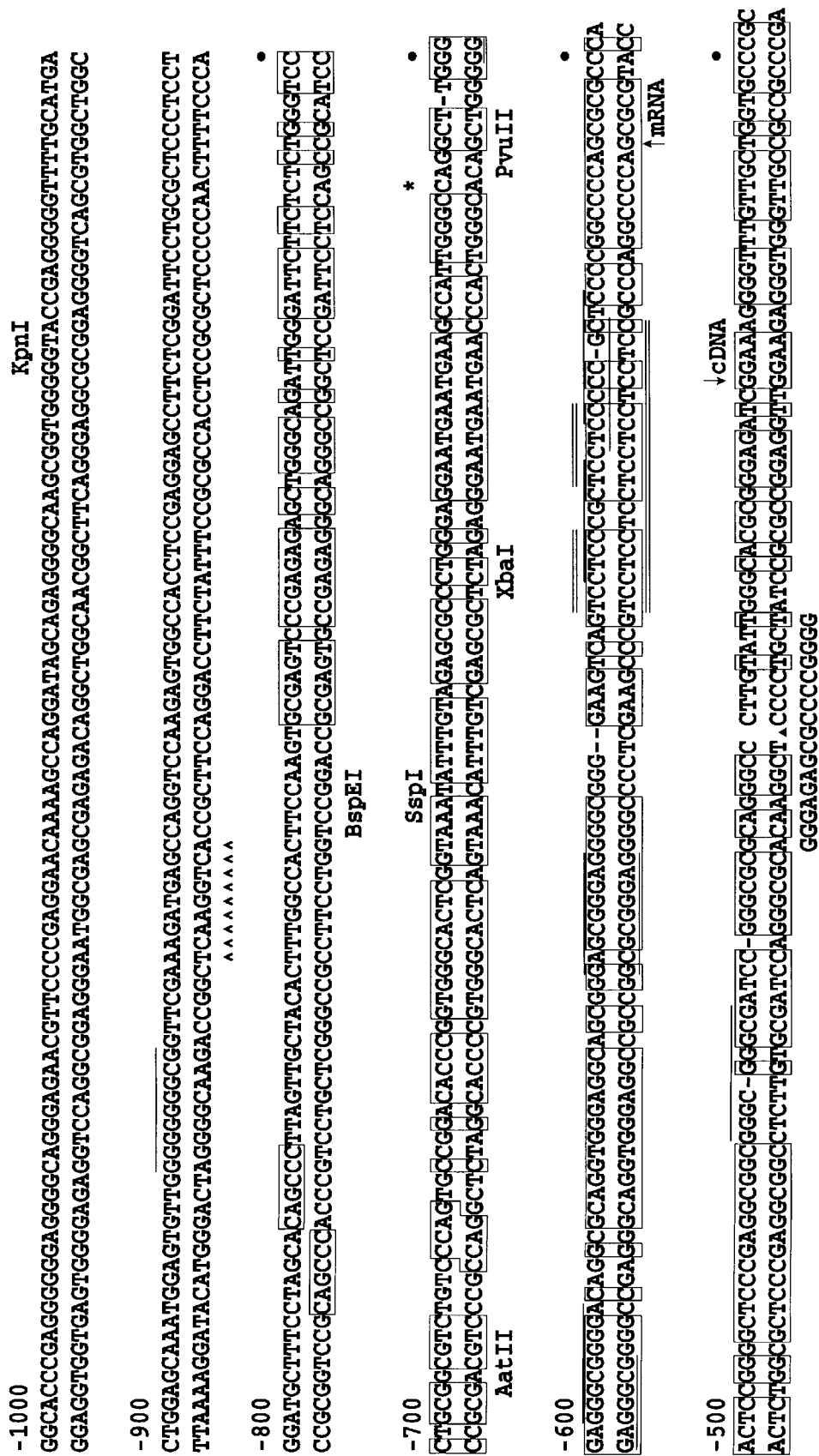
FIG. 1 shows the alignment of upstream sequences of the murine and human OP-1 gene. The murine sequence (bases 1299–2299 of SEQ ID NO: 2) is present in the upper sequence lines and the human sequence (bases 2326–3320 of SEQ ID NO: 1) is the lower sequence on all lines. The murine sequence is numbered backwards, counting back from the first ATG of the translated sequence which is shown highlighted. For purposes of alignment, dashes are introduced into the DNA sequence, and three portions of human DNP sequence have been cut from the sequence and placed underneath a gap, below a solid triangle.

As will be more fully described below, we have identified regions in the OP1 genetic sequence useful in identifying molecules capable of modulating OP-1 expression in vivo. Also as described herein, we have determined that OP-1 expression in vivo can be dependent both on cell type and on the status of the cell in a tissue. Specifically, as described herein below, OP-1 protein expression is differentially regulated in uterine tissue depending on the status of the uterine tissue. For example, OP-1 expression is dramatically down-regulated in uterine mouse tissue during pregnancy, whereas it is normally expressed in this tissue in virgin mice. Moreover, OP-1 expression in other tissues such as renal tissue apparently is unaffected during pregnancy. Administration of estrogen to a virgin mouse is capable of duplicating this down-regulation of OP-1 gene expression.

We investigated the DNA sequences responsible for the regulation of OP-1 gene expression by cloning non-coding sequences for the human and mouse OP-1 gene. The tissue specific modulation of OP-1 gene expression, and the significant homology which was found between an approximately 750 base region of human and murine 5' non-coding OP-1 genomic sequence, implicate these sequences as having utility in a method for the screening of compounds for their ability to modulate OP-1 expression.

In view of this disclosure and the examples provided below, a method for identifying molecules which can affect OP-1 expression in a particular cell type in vivo now is provided.

Cloning of Human and Mouse OP-1 Gene Non-coding Sequences In the Northern blot analysis of murine organs multiple OP-1 transcripts, are detected namely, three species of 1.8, 2.2, 2.4 kb and a prominent 4.0 kb RNA species (Özkaynak et al., 1992, J. Biol. Chem., 267:25220–25227; Özkaynak et al; Biochem. Biophys. Res. Comm., 179:116–123). The pattern is similar in rats with only the 1.8 kb species absent. The estrogen-mediated downregulation of OP-1 mRNA affects all of these species. In order to prove that the 4.0 kb mRNA is in fact a transcript from the same OP-1 locus, cDNA clones were isolated from a mouse teratocarcinoma cDNA library.

Four independent clones were obtained that added sequence information to the published mouse cDNA sequence. Two of these cDNA clones have longer 5'-untranslated sequences (0.4 and 0.3 kb) than previously reported (0.1 kb). Three of the murine clones contain additional 1.4 kb at the 3'-end. The combined sequences add up to a total OP-1 cDNA size of 3.5 kb, about 0.5 kb shorter than the 4.0 kb mRNA observed on Northern blots. cDNA clones that represent the 2 kb and 4 kb messages are shown schematically in FIG. 3a. Since the polyA-tail is lacking in those cDNA clones that extend the 3'-information, it was anticipated that missing 0.5 kb sequence occurs at the 3'-end.

In order to obtain the sequence immediately adjacent to the 3'-end of the 3.5 kb CDNA sequence, a mouse genomic library, ML1039J (Clontech), was screened with a 3'-end cDNA specific probe (0.45 kb, 3'-end XmnI-EcoRI fragment of murine DP-1 cDNA) according to the parameters described below for the cloning of upstream non-coding sequences. This screen yielded four lambda clones which were analyzed by Southern blotting. All clones yielded a 1.5 kb XmnI fragment which was subcloned from lambda Ö71 into a Bluescript vector and sequenced. Three polyadenylation signals (AATAAA) (Proudfoot et al, (1976) Nature, 263:211–214) were found in this genomic fragment, at 3.52-, 3.58-, and 3.59 kb (shown schematically in FIG. 3a by the *). The 3'-end cDNA and the genomic DNA sequences in the 1.5 kb XmnI fragment overlap by 0.4 kb in a region that immediately precedes the second polyadenylation signal located at 3.5 kb (FIG. 3a, region indicated by probe 6) and are in complete agreement within this stretch.

Human upstream non-coding sequence and additional mouse upstream non-coding sequence were obtained by screening human and mouse genomic libraries, HL1067J and ML1030J respectively (Clontech). All libraries were screened by an initial plating of 750,000 plaques (approximately 50,000 plaques/plate). Hybridizations were done in 40% formamide, 5× SSPE, 5× Denhardt's solution, and 0.1% SDS at 37° C. Nonspecific counts were removed in 0.1× SSPE, 0.1% SDS by shaking at 50° C. Human and mouse upstream genomic DNA sequences were obtained from clones lambda Ö3 and lambda Ö33, respectively (Clontech, HL1067J and ML1030J). These lambda clones were isolated using a $^{32}$P-labeled probe made from a human 0.47 kb EcoRI OP-1 cDNA fragment (obtained from pÖ115) containing mainly 5' non-coding and exon 1 sequences.

Figure 3A:
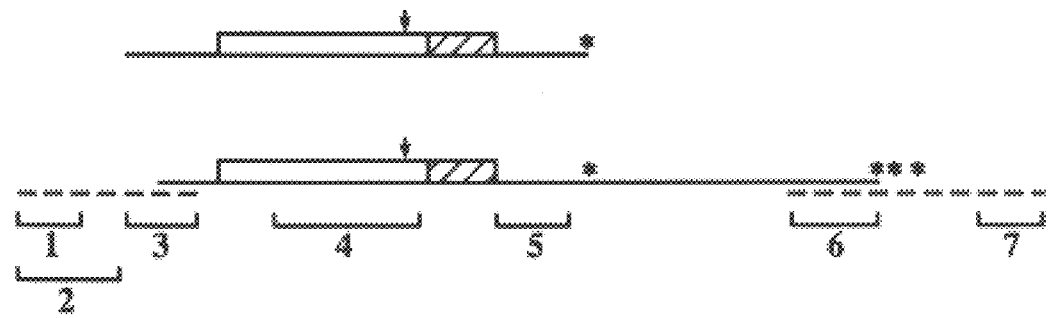
FIG. 3, Panel A shows a schematic of the 2 kb and 4 kb OP-1 mRNAs, the hybridization locations of probes 1 through 7 (indicated by the bars under the schematic). The solid line indicates OP-1 mRNA, the * indicate potential poly A signals, the boxes indicate the translated portion of OP-1 mRNA with the hatched box showing the TGF-β-like domain. The dashed lines indicate genomic DNA sequences. The arrows mark the locations of the cleavage site for OP-1 maturation.

A 7 kb EcoRI fragment from the human genomic clone, lambda Ö3, was isolated which contains 5 kb of upstream non-coding sequence. Additional upstream sequence information for murine was obtained by subcloning a 1.1 kb PstI fragment from the genomic phage clone lambda Ö33. This fragment overlaps with the 5'-end of the longest murine cDNA clone by 0.3 kb in the 5' non-coding region and provided 0.8 kb additional sequence information. A schematic diagram of the 2- and 4 kb OP-1 messages is shown in FIG. 3a with dashed lines indicating supplementing information derived from murine upstream and downstream genomic DNA.

All sequencing was done according to Sanger et al. (1977) Proc. Natl. Acad. Sci. 74:5463–5467, using exonuclease III-mediated unidirectional deletion (Özkaynak et al., (1987) BioTechniques, 5:770–773), subcloning of restriction fragments, and synthetic primers. Compressions were resolved by performing the reactions at 70° C. with Taq polymerase and using 7-deaza-GTP (U.S. Biochemical Corp., Cleveland, Ohio).

Verification of OP-1 mRNA Sequences by Northern Blotting

To verify the structures of the short and long mRNA species observed, Northern blot hybridizations were performed with probes made from seven non-overlapping DNA fragments (FIG. 3a; probes 1 through 7) specific to the 5' and 3' non-coding region, the protein coding sequence, and genomic regions upstream or downstream of the predicted mRNAs, respectively.

Figure 3B:
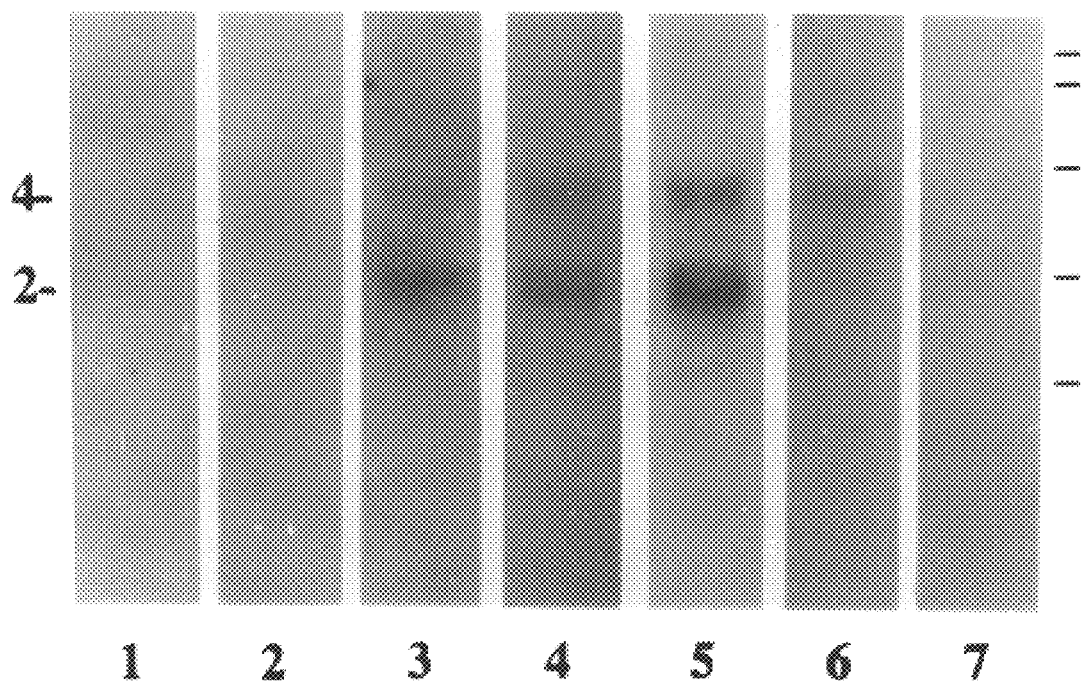

Hybridization of these probes to individual Northern blot strips containing mouse kidney mRNA is consistent with the predicted 4 kb mRNA structure. As shown in FIG. 3a, and FIG. 3b, the genomic DNA probes 1 and 2 did not hybridize to any message. Probe 2 is specific to the upstream sequences immediately adjacent to the cDNA. Probes 3, 4, and 5, specific to 5' non-coding, coding, and 3' non-coding regions, respectively, hybridized to both the 2 kb and 4 kb messages, hence these sequences are present in both messages. Probe 6, specific to sequences between the first and second polyadenylation signals, hybridized only to the 4 kb message. Finally, probe 7 which is specific to sequences further downstream of the fourth (last) polyadenylation signal, did not hybridize to any message. The results obtained with these probes confirm the two OP-1 mRNA structures and the approximate 5'- and 3'-end boundaries of OP-1 transcripts shown in FIG. 3a. This demonstrates that the 2 kb and 4 kb mRNA's are from the same OP-1 genomic locus rather than from multiple genes.

The extensive 3' sequence included in the 4 kb mFNA transcript suggests that the 3' untranslated sequence may play a role in OP-1 gene expression particularly as it has been detected across species namely, in mouse, rat, dog, human and chicken. Multiple stop codons in all three possible translation reading frames rule out the likelihood that this sequence encodes a peptide. The untranslated sequence itself may act therefore to influence mRNA stability. For example, the sequence may interact with another protein as has been described for transferrin receptor mRNA. Here, IRE-binding protein (IRE; iron response element) stabilizes the transferrin receptor mRNA by binding to the 3'-end of the mRNA (Standard et al., 1990, Genes Dev., 4:2157–2168, incorporated herein by reference). Alternatively, the 3'-end sequences may be interacting with the 5'-end sequences thereby affecting initiation of protein synthesis or, the 3'-end sequences may be serving as a binding site for other RNAs which can interfere with the binding of an expression in modulating molecule, including repressor molecule. (Klausner et al., 1989, Science, 246:870–872; Kozak, 1992, Ann. Rev. Cell Biol., 8:197–225, incorporated herein by reference).

Comparison of 5' Non-coding Sequences of Human and Mouse OP-1 DNA

The cloning of the 5' non-coding genomic murine and human OP-1 DNA sequences demonstrated that a high degree of sequence homology exists between the human and murine 5' non-coding DNA sequences. The homology extends from the base immediately upstream of the translation start site for the OP-1 morphogen protein to approximately 750 bases upstream of the translation start site, as is shown in the shaded regions of FIG. 1, with the murine sequences being the upper lines and the human sequences being the lower lines. The 5' nucleotide of the region of homology for the human OP-1 5' non-coding sequence is base 2548 of Seq. ID No. 1 and for the murine OP-1 5' non-coding sequence is bases 1549 of Seq. ID No. 2. The significant homology between the human and murine 5' non-coding sequences of OP-1 suggest that this region may be important in the regulation of OP-1 expression. As will be discussed in more detail below, this region contains several conserved DNA sequences which have been identified as the DNA binding sequences for two DNA binding proteins, Wt-1 and Egr-1, which both recognize these DNA sequences. The DNA binding sequences for Wt-1/Egr-1 present in human and murine are marked in FIG. 1 with a single line. Also, the TCC binding sequence, a DNA binding sequence for Wt-1 and Egr-1, is marked in FIG. 1 by the double line. WT-1 and Egr-1 proteins have also been implicated in the regulation of expression of several genes which are unrelated to OP-1.

Figure 1B:
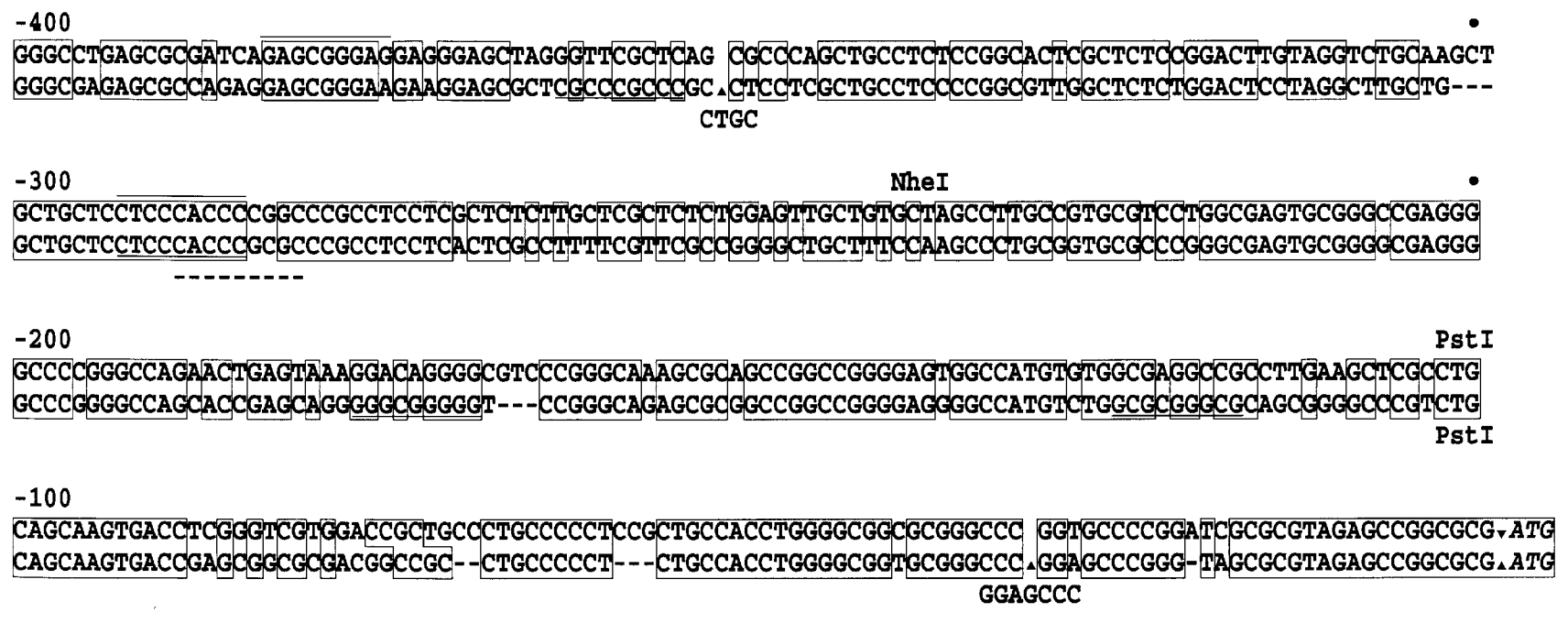

Alignments of mouse and OP-1 human genomic sequences reveals a conserved stretch of 0.75 kb just upstream of the first ATG that contains several patterns with marked similarity to the zinc-finger protein binding sequence (5'-GCG GGG GCG-3') specific for Egr-1 and Wt-1 (Christy et al., 1989, PNAS, 86:8737–8741; Rauscher et al., 1990, Science, 250:1259–1262; Drummond et al., 1992, Science, 257:664–678). In mouse, a total of 8, and in human 7, patterns, conforming to the degenerate Egr-1/Wt-1 binding sequence (5'-GNG NGG GNG-3') (Rupprecht et al., 1994, J. Biol. Chem., 269: 6198–6202; Werner et al., 1994, J. Biol. Chem., 269: 12940–12946 are located before and after the presumed transcriptional initiation site (FIG. 1, shown by solid single lines). The presence of these has significance in light of the elevated levels of Wt-1 mRNA in the rat uterus decidua during pregnancy (Zhou et al., 1993, Differentiation, 54:109–114).

The analysis also revealed, in the human upstream region, a pattern of seven TCC repeats, present at –561, immediately 3' of two Egr/Wt-1 sequences (at –624 and –587) (FIG. 1, shown by double solid lines and at position 2758–2778 of Seq. ID No. 1). The mouse upstream region contains a similar, albeit less obvious sequence at –356 and at position 1755–1769 of Seq. ID No. 2. This TCC-repeat pattern is found in the promoters of PDGF-A and several other growth-related genes, and Wt-1 has been found to activate transcription when either of the sequences are present and to suppress it when both sequences are present. (Wang et al., 1992, Biochem. Biophys Res. Comm., 188:433–439; Wang et al. 1993, PNAS, 90:8896–8900 incorporated herein by reference). Accordingly, estrogen receptor may exert its effect on OP-1 expression in uterus by upregulating Wt-1, either directly or indirectly. Alternatively or, in addition other regulatory elements, located further upstream of the OP-1 gene may be involved in estrogen regulation.

Also on FIG. 1, the human 5' non-coding DNA sequence is shown to contain a Fushi-tarazu (FTZ) binding sequence which is marked by carats below the human DNA sequence. A FTZ binding sequence is bound by the Fushi-tarazu protein (FTZ-F1), which is a member of the superfamily of nuclear receptors (Parker, (1993) *Current opinion in Cell Biology,* 5:499–504, ). The superfamily of nuclear receptor proteins include steroid hormones, retinoids, thyroid hormone, nerve growth factor and Fushi-tarazu, and are structurally related. FTZ-F1 is likely to belong to a subfamily of nuclear receptors that bind DNA as monomers.

The FTZ-F1 protein is a positive regulator at the fushi-tarazu gene in blastoderm stage embryos of Drosophila . FTZ-F1 is closely related in the silkworm (Bombyx) BmFTZ-F1 protein and the mouse embryonal long terminal repeat binding protein (ELP) and all of them are members of the nuclear hormone receptor superfamily, which recognizes the same 9 base pair sequence, 5'-PyCAAGGPyCPu-3'. The FTZ binding sequence does not apparently have a direct or inverted repeat. In contrast, other members of the nuclear hormone receptor superfamily usually bind to repeated sequences. Nevertheless, the FTZ-F1, BmFTZ-F1 and ELP proteins have high affinities for the FTZ binding site DNA, indicating that the mechanism that the binding is somewhat different from that of other members of the nuclear hormone receptor superfamily. (Hitachi et al., 1992, *Mol. and Cell Biology December, pp.* 5667–5672.).

The mRNA transcription initiation site for human OP-1 is marked on FIG. 1 by the upward arrow, and the OP-1 protein translation initiation site is marked on FIG. 1 by the solid triangles just prior to the highlighted ATG. The transcription initiation site for the human OP-1 gene is at base 2790 of Seq. ID No. 1 and the analogous site for murine is at base 1788 of Seq. ID No. 2. The translation initiation site for the human OP-1 gene is at base 3318 of Seq. ID No. 1 and for murine it is at base 2296 of Seq. ID No. 2. The high degree of identity that the murine and human DNA sequences share in the region between the transcription initiation site and the translation initiation site, suggests that this region likely plays a role in the modulation of the expression of the OP-1 gene product.

Analysis of OP-1 Gene Expression in Mouse Tissues

A detailed analysis of the uro-genital tract of rats has revealed OP-1 mRNA expression in the renal (kidney), and bladder tissues, as well as at other sites of the urogenital organ system. The most abundant levels are present in renal and uterine tissue (8 week old mice), while much lower levels were found in ovaries. The mRNA level of G3DPH, a "housekeeping function" molecule, was used as an internal control for recovery and quality of mRNA preparations and equal amounts of poly(A)+ RNA (5 mg), were loaded into each lane.

Preparation of RNA and Northern blot hybridization analysis was conducted as follows. 8-week-old female mice, strain CD-1, were obtained from Charles River Laboratories, Wilmington, Mass. Total RNA, from the various organs of mice was prepared using the acid-guanidine thiocyanate-phenol-chloroform method (Chomczynski et al., (1987) Anal. Biochem. 162:156–159). The RNA was dissolved in TES buffer (10 mM Tris-HC1, 1 mM $Na_2$-EDTA, 0.1% SDS, pH7.5) containing Proteinase K (Stratagene, La Jolla, Calif.; approx. 1 mg proteinase /ml TES) and incubated at 37° C. for 1 hr. Poly $(A)^+$ RNA was selected in a batch procedure on oligo(dT)-cellulose (Stratagene, La Jolla, Calif.) in 0.5 M NaCl, 10 mM Tris-HCl, 1 mM $Na_2$-EDTA, pH 7.4 (1× binding buffer). For the selection of poly (A)+ RNA, total RNA obtained from 1 g of tissue was mixed with approximately 0.1 g of oligo(dT)-cellulose (in 11 ml TES containing 0.5 M NaCl). The tubes containing the RNA and oligo(dT)-cellulose were gently shaken for approx. 2 hrs. Thereafter, the oligo(dT)-cellulose was washed twice in lx binding buffer and once in 0.5× binding buffer (0.25 M NaCl, 10 mM Tris-HCl, 1 mM $Na_2$-EDTA, pH 7.4) and poly (A)+ RNA was eluted with water and precipitated with ethanol.

Poly(A)+ RNA (5 mg per lane) was electrophoresed on 1.2% agarose-formaldehyde gels with 1 mg of 400 µg/ml ethidium bromide added to each sample prior to heat denaturation (Rosen et al., (1990) Focus, 12:23–24). Electrophoresis was performed at 100 Volts with continuous circulation of the 1×MOPS buffer (Ausubel et al., eds., (1990) *Current Protocols in Molecular Biology*, John Wiley & Sons, New York). Following electrophoresis, the gels were photographed, rinsed briefly in water, and blotted overnight onto Nytran (Schleicher & Schuell Inc., Keene, N.H.) or Duralon-UV (Stratagene) membranes in 10× SSC. The membranes were dried at 800 for 30 min. and irradiated with UV light (1 mW /cm for 25 sec.).

The $^2$P-labeled probe was made from a murine OP-1 cDNA fragment (0.68 kb BstXI-BGlI frg.) by random hexanucleotide priming (Feinberg et al., (1984) Anal. Biochem., 137:266–267). The hybridizations were done in 40% formamide, 5× SSPE, 5× Denhardt's, 0.1% SDS, pH 7.5 at 37° C. overnight. The non-specific counts were washed off by shaking in 0.1× SSPE, 0.1% SDS at 50° C. For re-use, filters were stripped in 1 mM Tris-HCl, 1 mM $Na_2$-EDTA, 0.1% SDS, pH 7.5 at 80° C. for 10 min.

Analysis of OP-1 Expression During Pregnancy in Mice

An examination of the effect of pregnancy upon OP-1 expression was undertaken by measuring OP-1 mRNA levels in kidney, ovary and uterus, before, during, and after pregnancy (virgins, 2-day post-coital (pc), 4-day pc, 6-day pc, 8-day pc, 13 day pc, 17-day pc, 3-day lactating, and retired breeders) by Northern blot hybridization of poly(A)+ RNA. These measurements demonstrated that, while kidneys show no pregnancy-related changes in OP-1 mRNA levels, the uterine levels became nearly undetectable by 6-day pc. However, no changes were observed in the ovaries. A dramatic and rapid decline in OP-1 message in uterine tissue between day 3 and 4 of pregnancy is apparent in the comparison with virgin animals.

The levels of OP-1 mRNA in the embryo and maternal levels in uterus of 8 week old mice at day 13 and 16 of the pregnancy were also compared. While the OP-1 expression in the pregnant uterus is dramatically reduced, high levels of OP-1 message are found in the mouse embryo at 13- and 16-days. Thus, at a stage of pregnancy when OP-1 mRNA expression in the maternal uterus is almost undetectable, embryonal OP-1 expression is high. The high embryonal OP-1 expression also is detected consistent with the relatively high levels of OP-1 mRNA, found in human placenta. The level of OP-1 mRNA measured in the embryo is in the same range as that measured in adult kidney or virgin uterus tissue. Hence, it is likely that OP-1 plays a critical role in the development of the embryo which may require appropriate amounts of OP-1 at very specific stages of tissue and organ morphogensis. While not being limited to any given theory, it is possible that OP-1 expression in uterine tissue during pregnancy potentially could interfere with the level of OP-1 produced by the developing embryo, and thereby interfere with proper development of the embryo. Therefore, a shutdown or inhibition of uterine OP-1 expression during pregnancy might be for the benefit of the fetus.

Effect of Estrogen and Progesterone on OP-1 Expression

During pregnancy the estrogen and progesterone levels increase many fold and high levels are sustained until birth.

To determine whether these hormonal changes are responsible for the altered OP-1 transcription in pregnant uterine tissue, non-pregnant female mice were subcutaneously administered 17β-estradiol, or progesterone, or a combination of both.

In the first experiment the rapid increase in estrogen and progesterone levels during pregnancy was simulated. Non-pregnant mice were injected subcutaneously on four consecutive days with increasing doses, starting with 20 mg 17β-estradiol, or 100 mg progesterone or the combination of both and doubling the dose on each following day. On the fourth day the animals were sacrificed and mRNA was isolated from uteri and kidneys. A striking negative effect of 17β-estradiol on the uterine OP-1 mRNA expression was observed, but no effect by progesterone was seen. In the kidneys, however, mRNA levels did not change after 17β-estradiol or progesterone treatment.

Figure 2:
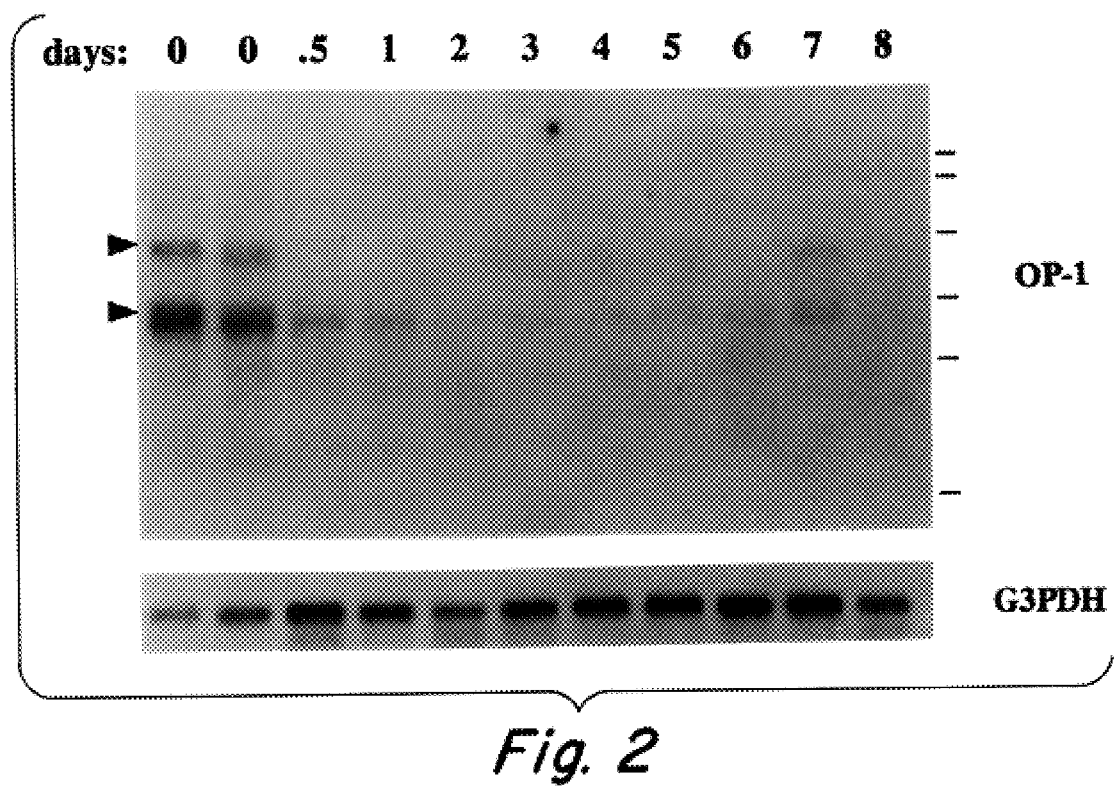
FIG. 2 shows a time course of murine uterus OP-1 mRNA regulation by estrogen.

Another experiment addressed the time course: 17β-estradiol was administered to virgin female mice at a constant dose of 200 mg (50 ml of 4 mg/ml 17β-estradiol per day, subcutaneously in DMSO [dimethyl sulfoxide]+150 ml 150 mM NaCl) (FIG. 2) Following this, their uteri were extracted, poly(A)+ RNA was prepared, equal amounts of poly(A)+ RNA (5 mg) was loaded into each lane of a 1.2% agarose-formaldehyde gel and analyzed by Northern blot hybridization. The effect was rapid, with considerable decrease of OP-1 mRNA 12 hours after administration of 17β-estradiol and almost undetectable levels by 48 hours, as shown in FIG. 2. In the figure, the lanes correspond as follows: from left to right, 0-day (negative control), 0-day (negative control), 0.5-, 1-, 2-, 3-, 4-, 5-, 6-, 7-, and 8-days. The arrowheads mark the two major OP-1 mRNA species. A modest amount of message reappears a few days later (FIG. 2).

The uterus has been identified as a major site of OP-1 expression. The level of OP-1 expression in uterine tissue is comparable to that observed in renal tissue. However, during pregnancy, by day four, the uterine OP-1 mRNA levels are reduced to the limit of detection. The loss of OP-1 expression corresponds with also is rising levels of estrogen during this same time frame. The same dramatic loss of uterine OP-1 message also is observed in estrogen-treated animals, suggesting that estrogen is involved in negative regulation of OP-1 expression in uterine tissue. The effect of estrogen is rapid, with most of the message disappearing after 12 hours of 17β-estradiol administration. The reappearance of some OP-1 message at later days may be due to a counter-regulatory mechanism. In contrast to the modulated OP-1 mRNA levels in the uterus, no substantial changes occur in renal tissue during pregnancy or in response to estrogen treatment. Therefore, OP-1 mRNA expression in these different organs is regulated independently. The differential expression may be due, for example, to a lack of estrogen receptors in renal tissue. Alternatively, co-regulation by means of one or more accessory molecules that interact with estrogen or a related nuclear receptor molecule(s) may allow for the independent regulation. For example, each of Wt-1 protein (which binds to the Wt-1/Egr-1 element) and OP-1 protein are required for normal kidney development, and each are expressed at high levels during kidney tissue development. As described above the OP-1 promoter region contains Wt-1 consensus binding elements. Wt-1 protein also has been shown to negatively regulate the transcription of the insulin growth factor II gene and the platelet-derived growth factor A chain gene. Kreidberg et al., Cell, 1993, 74:679–691. Without being limited to a given theory, it may be that Wt-1 protein, either alone or in combination with one or more molecules is involved in the expression of OP-1. For example, Wt-1 protein may act in concert with a nuclear hormone receptor element, including, for example, the estrogen receptor element.

Implications of Tissue Specific Differential Regulation of OP-1 Expression

Estrogen also has been shown to inhibit the uterine expression of calbindin-$D_{28k}$, a vitamin D dependent calcium binding protein, the α-subunit expression of the glycoprotein hormones, and other proteins involved in bone formation. Estrogen also has been shown to cause dramatic decreases in the steady state mRNA levels of the bone matrix proteins osteocalcin, prepro α2(I) chain type I collagen, osteonectin, osteopontin, and alkaline phosphatase in an ovariectomized rat, which is a rat model for osteoporosis.

Estrogen appears to mediate its beneficial effect on bone metabolism in the osteoporotic model through inhibition of osteoclasts. Estrogen does not reverse osteoporosis. By contrast, OP-1, which is expressed in uterine, renal and bone tissues, is able to induce an increase in bone mass in the osteoporotic model. Thus, the negative effect of estrogen on OP-1 expression in uterine tissue may seem unexpected in view of estrogen's effect on bone metabolism.

In addition to the 5' non-coding DNA sequences of OP-1, the other non-coding sequences such as introns and 3' non-coding sequences may be involved in the modulation of OP-1 protein expression. This invention presents a method in which these non-coding sequences are assayed while in operative association with a reporter gene for their influence on the expression of OP-1. Non-coding sequences which are involved in the modulation of OP-1 expression will be identified by culturing cells transfected with the non-coding sequences, in operative association with a reporter gene, with one or more compound(s), measuring the level of reporter gene expression, and comparing this level of expression to the level of reporter gene expression in the absence of the compound(s).

EXEMPLARY CELLS, VECTORS, REPORTER GENES AND ASSAYS FOR USE IN SCREENING COMPOUNDS WHICH MODULATE OP-1 REGULATORY SEQUENCES

I. Useful Cells

Any eukaryotic cell, including an immortalized cell line suitable for long term culturing conditions is contemplated to be useful for the method and cell of the invention. Useful cells should be easy to transfect, are capable of stably maintaining foreign DNA with an unrearranged sequence, and have the necessary cellular components for efficient transcription and translation of the protein, including any elements required for post-translational modification and secretion, if necessary. Where the cell is to be transfected with a non-dominating selection gene, the cell genotype preferably is deficient for the endogenous selection gene. Preferably, the cell line also has simple media composition requirements, and rapid generation times. Particularly useful cell lines are mammalian cell lines, including myeloma, HeLa, fibroblast, embryonic and various tissue cell lines, e.g., kidney, liver, lung and the like. A large number of cell lines now are available through the American Type Culture Collection (Rockville, Md.) or through the European Collection of Animal Cell Cultures (Porton Down, Salisbury, SP4 0 JG, U.K.)

Where, as here, the expression of a reporter gene that is controlled by non-coding sequences of the morphogen OP-1 is to be analyzed, particularly useful cells and cell lines are envisioned to include eukaryotic, preferably mammalian cells of a tissue and cell type known to express OP-1 and/or closely related proteins. Such cells, include, without limitation, cells of uro-genital cell origin, including kidney, bladder and ovary cells, lung, liver, mammary gland and cardiac cells, cells of gonadal origin, cells of gastrointestinal origin, glial cells and other cell lines known to express endogenous genes encoding morphogenic proteins. Preferred cell lines are of epithelial origin.

II. Exemplary Vectors/Vector Construction Considerations

Useful vectors for use in the invention include, but are not limited to cosmids, phagemids, yeast artificial chromosomes or other large vectors. Vectors that can be maintained within the nucleus or integrated into the genome by homologous recombination are also useful. For example a vector such as PSV2CAT would be useful.

Selected portions of non-coding OP-1 sequence car be cloned into a useful vector using standard molecular cloning techniques, as will be apparent to one of ordinary skill in the art. Restriction endonuclease sites will be utilized when possible, and can be engineered into the sequence when needed. If restriction endonuclease sites are needed to be engineered into the sequence, eight base recognition sites are preferable because they generally occur infrequently in DNA and will enhance a practitioners ability to obtain the sequence of interest. Restriction endonuclease sites can be engineered into the non-coding sequence using the common techniques such as site directed mutagenesis arid PCR with primers including the desired restriction endonuclease site.

As discussed above, murine and human OP-1 sequences share a region of high homology covering approximately 750 bases upstream of the translation initiation site as shown by the shading in FIG. 1. This region is positions 2548–3317 of Seq. ID No. 1 and positions 1549–2296 of Seq. ID No. 2. The mRNA transcription initiation site lies within this region at position 2790 of Seq. ID No. 1 and by analogy at position 1788 of Seq. ID No. 2, shown in FIG. 1 by the upward arrow. This suggests that positions 2548–2790 of Seq. ID No. 1 and 1549–1788 of Seq. ID No. 2 contain conserved promoter elements for the expression of OP-1 mRNA, and approximately 500 bases at positions 2791–3317 of Seq. ID No. 1 and positions 1790–2296 of Seq. ID No. 2 contain conserved elements of the transcribed, but not translated, sequences all or part of which may be involved in the regulation of OP-1 expression. Additionally sequences upstream of the homology region may also be involved in the regulation of OP-1 expression. Thus a range of upstream sequences, including sequences upstream of the transcription initiation site and not including the approximately 500 bases of transcribed sequence, can be fused in operative association with a reporter gene to modulate expression of the gene.

3' non-coding sequences and intron sequences also can be fused in operative association with a reporter gene, either separately or in combination with each other or with 5' non-coding sequences. For example, one can place the 5' sequences defined by positions 2790–3317; 2548–2790 or 2548–3317 of Seq. ID No. 1, and either/both of 3' sequences or intron sequences in operative association with a reporter gene. The positions of the six introns are shown in Seq. ID No. 1 as bases 3736 to 10700; bases 10897 to 11063; bases 11217 to 11424; bases 11623 to 13358; bases 13440 to 15048; bases 15166 to 17250.

Also envisioned is a nucleic acid construct comprising a small fragment of 5' non-coding OP-1 sequence in combination with additional conserved elements such as one or more Wt-1/Egr-1 binding sequences; a TCC binding sequence and/or a FTZ binding sequence in operative association with a reporter gene. Such a nucleic acid construct also could include intron sequences and/or 3' non-coding sequences.

A range of useful 5' non-coding fragments has been provided, and as will be apparent to those of ordinary skill in the art, smaller fragments of OP-1 sequence also are useful. Such smaller fragments can be identified to deleting bases from one or both ends of the provided 5' non-coding fragments, using techniques that are well known in the art and testing the truncated constructs for their ability to modulate reporter gene expression. In this way, the shortest modulating sequences can be identified.

III. Transfection Considerations

Any method for incorporating nucleic acids into cells of interest is contemplated in the method of the invention. Calcium phosphate ($CaPO_4$), followed by glycerol shock is a standard means used in the art for introducing vectors, particularly plasmid DNA into mammalian cells. A representative method is disclosed in Cockett et al., (1990) *Biotechnology* 8: 662–667, incorporated herein by reference. Other methods that may be used include electroporation, protoplast fusion, particularly useful in myeloma transfections, microinjections, lipofections and DEAE-dextran mediated uptake. Methods for these procedures are described in F. M. Ausubel, ed., *Current Protocols in Molecular Biology*, John Wiley & Sons, New York (1989).

As will be appreciated by those having skill in the art, optimal DNA concentrations per transfection will vary according to the transfection protocol. For calcium phosphate transfection, for example, preferably 5–10 µg plasmid DNA per plasmid type is transfected. In addition, the DNA to be transfected preferably is essentially free of contaminants that may interfere with DNA incorporation. A standard means used in the art for purifying DNA is by ethidium bromide banding.

IV. Exemplary Reporter Genes

There are numerous reporter systems commercially available, which include, without limitation, the chloramphenicoL acetyltransferase (CAT), luciferase, GAL4, and the human growth hormone (hGH) assay systems.

CAT is a well characterized and frequently used reporter system and a major advantage of this system is that it is an extensively validated and widely accepted measure of promoter activity. See, for example, Gorman, C. M., Moffat, L. F., and Howard, B. H. (1982) *Mol. Cell. Biol.*, 2:1044–1051 for a description of the reporter gene and general methodology. In this system cells are harvested 2–3 days after transfection with CAT expression vectors and extracts prepared. The extracts are incubated with acetyl CoA and radioactive chloramphenicol. Following the incubation acetylated chloramphenicol is separated from nonacetylated form by thin layer chromatography. In this assay the degree of acetylation reflects the CAT gene activity with the particular promoter.

Another well-recognized reporter system is the firefly luciferase reporter system. See, for example Gould, S. J., and Subramani, S. (1988) *Anal. Biochem.*, 7:404–408 for a description of the reporter gene and general methodology. The luciferase assay is fast and has increased sensitivity. The system also is particularly useful in bulk transfections or if the promoter of interest is weak. In this assay transfected cells are grown under standard conditions, and when cultured under assay conditions both ATP and the substrate luciferin is added to the cell lysate. The enzyme luciferase catalyzes a rapid, ATP dependent oxidation of the substrate which then emits light. The total light output is measured using a luminometer according to manufacturer's instructions (e.g., Cromega) and is proportional to the amount of luciferase present over a wide range of enzyme concentrations.

A third reporter system is based on immunologic detection of hGH, it is quick and easy to use. (Selden, R., Burke-Howie, K. Rowe, M. E., Goodman, H. M., and Moore, D. D. (1986), *Mol. Cell. Biol.,* 6:3173–3179 incorporated herein by reference). hGH is assayed in the media, rather than in cell extracts. This allows direct monitoring over by a single population of transfected cells over time.

As indicated above and as will be appreciated by those having ordinary skill in the art, particular details of the conventional means for transfection, expression, and assay of recombinant genes are well documented in the art and are understood by those having ordinary skill in the art. The instant invention enables and discloses vectors, cells and a method for screening compounds to determine the capability of compounds to modulate the expression of OP-1 via the non-coding sequences of the OP-1 genomic DNA.

Further details on the various technical aspects of each of the steps used in recombinant production of foreign genes in mammalian expression systems can be found in a number of texts and laboratory manuals in the art, such as, for example, F. M. Ausubel et al., Ed., *Current Protocols in Molecular Biology*, John Wiley & Sons, New York, (1989).

VIII. Exemplary Homologous/Non-Homologous Recombination

One approach to screen for inducers of (organ-specific) OP-1 expression in a particular cell line derived from a particular tissue such as renal or uterine tissue, is through gene targeting by homologous recombination (Sedivy et al., W.H. Freeman & Co., New York (1992); A. S. Waldman, crit. Rev. Oncol. Hematol. 12, 49 (1992)). In one strategy the endogenous (genomic) OP-1 gene is replaced by another reporter gene which is optimally suited for screening assays, such as the firefly luciferase gene. To target the OP-1 gene in an appropriate cell line, e.g., a kidney cell line or NBT-2, the following arrangement of genetic elements can be assembled.

Genomic OP-1 upstream and promoter sequences preferably 3000 to 5000 nucleotides in length, and which mediate the homologous recombination, are attached to the luciferase gene. The OP-1 upstream sequences down to the first coding ATG can be attached at the start codon ATG of the luciferase coding sequence, using a restriction site such as NcoI, which can be introduced by site directed mutagenesis into both the promoter and the laciferase sequences.

Also included is a selective marker, preferably the neo gene, without its own promoter. Preferably, selectable marker (neo) is placed downstream of the reporter gene (luciferase), after an intercistronic sequence derived from the poliovirus genome and which allows translation of the sequence marker on the same transcript as the reporter gene transcripts. Details of this approach, including specific intercistronic sequences and the detailed steps of homologous recombination, are described in the art, including (Jasin et al., *PNAS USA* 85:8583 (1988); Sedivy et al., *PNAS USA* 86, 227 (1989); Dorin et al., *Science* 243:1357 (1989) the disclosures of which are incorporated herein by reference. As described therein, the endogenes OP-1 gene is replaced by the luciferase and neo coding sequences and the expression of these sequences then asayed in a standard A screening protocol.

A genetic arrangement of OP-1 promoter (as much genomic OP-1 upstream sequence as possible, up to 10,000 bp) and reporter gene (without its original promoter but joined directly to the OP-1 ATG or in its vicinity) can also be introduced into cells on standard eukaryotic expression vectors. These vectors carry selectable markers (neo, dhfr, etc.) and will typically be integrated into the host genome with variable copy number ranging from one to several copies without efforts at amplification. Also, if desired, the vector or gene copy number can be enhanced using a well characterized amplifiable gene, such as dhfr in conjunction with methotrexate. Commercial vectors designed for autonomous replication without integration are readily available. One source vector is the Episomal Expression Epstein Barr Virus Vector (pREP, Invitrogen Corp., San Diego Calif.).

Introns also can be tested for regulatory sequences as described hereinabove using the methods described herein. One or more intron sequences derived from a genomic OP-1 locus preferably is introduced into proper mammalian cells using, for example, a yeast artificial chromosome (pYACneo, Clontech, Inc. Palo Alto, Calif.) (Ref. Albertson, H. M. et al. PNAS USA, 87:4256, 1990), or other vectors adapted to allow transfer of large sequences, e.g., up to 1 megabases. As for the OP-1 5' or 3' noncoding sequences described above, the intron sequence or a portion thereof is incorporated in operative association with a reporter gene and the ability of the sequence to modulate reporter gene expressions then associated.

X. Exemplary Screening Assay for Compounds which Alter OP-1 Gene or Reporter Gene Levels Candidate compound(s) which may be administered to affect the level of a given endogenous morphogen, such as OP-1, or a reporter gene that is fused to OP-1 non-coding sequence may be found using the following screening assay, in which the level of reporter gene production by a cell type which produces measurable levels of the reporter gene expression product by incubating the cell in culture with and without the candidate compound, in order to assess the effects of the compound on the cell. This can be accomplished by detection of the reporter expression product either at the protein or RNA level. The protocol is based on a procedure for identifying compounds which alter endogenous levels of morphogen expression, a detailed description also may be found in PCT US 92/07359.

Cultured cells are transfected with portions of OP-1 non-coding sequences in operative association with a reporter gene, and such transfected cells are maintained with the vector remaining as a plasmid in the cell nucleus or the vector can be integrated into the host cell genome, preferably at the OP-1 genomic locus.

Cell samples for testing the level of reporter gene expression are collected periodically and evaluated for reporter gene expression using the appropriate assay for the given reporter gene as indicated in the section describing reporter gene assays, or, alternatively, a portion of the cell culture itself can be collected periodically and used to prepare polyA(+) RNA for mRNA analysis.

Once candidate compounds are identified, they can be produced in reasonable, useful quantities using standard methodologies known in the art. Amino acid-based molecules can be encoded by synthetic nucleic acid molecules, and expressed in a recombinant expression system as described herein above or in the art. Alternatively, such molecules can be chemically synthesized, e.g., by means of an automated peptide synthesizer, for example. Non-amino acid-based molecules can be produced by standard organic chemical synthesis procedures.

Provided below is an exemplary protocol for carrying out the method of the invention, using the CAT gene as the reporter gene and one or more mammalian cell lines known to express OP-1. The example is non limiting, and other cells, reporter genes and OP-1 non-coding sequences are envisioned.

Exemplary Construction Of Representative Vectors For Transfections

A DNA fragment containing the OP-1 promoter can be joined to a reporter gene for transfection into a cell line that expresses endogenous OP-1. Suitable cell lines are selected by Northern blot hybridization to an OP-1 specific probe (by analyzing the cell extracts for OP-1 mRNA). Using this technology we have found several cell lines which make high levels of OP-1 mRNA, and some of these lines are the kidney line IMCD, the bladder Line NBT II.

An approximately 5 Kb EcoRI, BamHI genomic fragment containing approximately 4 Kb of upstream OP-1 sequences as well as part of the first intron is blunt-ended with T4 DNA polymerase and cloned into a polylinker of a pUC vector (pO146-1). An approximately 3.5 kb DNA fragment containing human OP-i upstream sequences is obtained by deleting a portion of coding sequences and the first intron from pO146-1 with the restriction enzyme EheI. The ~3.5kb fragment has blunt ends and contains mostly 5' non-coding sequences and also includes a short stretch of 30 bases into the OP-1 gene. This upstream fragment is of ~3.5kb ligated to a 1.6 kb HindIII-BamHI fragment from the CAT gene obtained from the vector SV2CAT by 5' HindIII end blunted ligation. The 1.6 kb CAT gene fragment contains about 70 bases of upstream sequences. These ligated fragments are cloned into Bluescript KS(-) vector (Stratgene, La Jolla, Calif.). This construct in turn is subjected to site specific mutagenesis to delete the extra sequences (approximately 30 bases) from the 3' end of the OP-1 upstream sequences and the adjacent 5' non-coding sequences (approximately 70 bases) from the CAT gene. This mutagenesis results in the elimination of any OP-1 coding sequences from the promoter fragment as well as any non-coding sequences upstream of the CAT gene. Thus the resulting construct is a fusion of OP-1 upstream sequences with the CAT gene sequences which encode the CAT protein. This approximately 5 kb fragment is then excised from Bluescript using HindIII and BamHI and ligated into a HindIII-BamHI cut and gel purified back-bone of the pSV2CAT vector, for transfection into suitable cell lines.

Suitable cell lines include cell lines that have been shown to contain high levels of OP-1 mRNA, indicating that the OP-1 promoter is active in the cells. Two of these cell lines are mouse inner medullary collecting duct (IMCD) cells, and the rat bladder carcinoma line (NBT II). However other cell lines of the uro-genital system that produce high levels of the OP-1 message can be used in addition to the many previously mentioned cell types and cell lines.

The transfection of this vector into an OP-1 producing cell line is accomplished following standard techniques, i.e., transfection using calcium phosphate, liposome mediated transfection, electroporation, or DEAE-dextran transfection.

The transfected cells are harvested 48–72 hours alter transfection with the CAT expression vector and extracts are made by successive freeze-thawing. 2 $\mu$l of 200 $\mu$Ci/ml 14C-choramphenicol (35 to 55 mCi/mmol), 20 $\mu$l of 4 mM acetyl CoA, 32.5 $\mu$l of 1 M Tris-HCl, pH 7.5, and 75.5 $\mu$l of water is added to 20 ml of cell extract, and incubated for 1 hour at 37 degrees Celsius. Upon completion of incubation, 1 ml ethyl acetate is added to the reaction, microcentrifuged for 1 minute and the top layer is removed. This top layer is dried down in a SpeedVac for 45 minutes, and each sample is resuspended in 30 ml of ethyl acetate. The samples are spotted onto a plastic-backed TLC sheet for chromatography. The thin layer is then developed in a tank containing 200 ml of 19:1 chloroform/methanol. The chromatography is run for 2 hours and placed under film for autoradiography.

The activity of the $C^{14}$ in the monoacetylated chloramphenicol series is calculated as described in Current Protocols in Molecular Biology, 1993 (Ausubel et al., eds. John Wiley & Sons, New York).

Upon determination of CAT activity, the main construct can be deleted in sections to determine the regions that are responsible for the observed CAT activity. Alternatively, the upstream sequences can be deleted unidirectionally, using an exonuclease such as Bal31, and the deletion product can be analyzed in the CAT activity assay. This system can also be used in the method of the invention to screen compounds for their ability to modulate OP-1 expression by dividing the cells into several groups, and culturing one group in the absence of any added compounds, and culturing the other groups with one or more candidate compound, and comparing the resulting levels of CAT activity.

While a readily assayable, well characterized, non OP-1 reporter gene is preferred in the method disclosed herein, as will be appreciated by those having ordinary skill in the art, OP-1 coding sequence also may be used in the screening method of the invention. The OP-1 expression preferably is determined by an immunoassay or by Northern or dot blot or other means for measuring mRNA transcript. See, for example, WO 95/1L983, published May 4, 1995 for a detailed description on assaying changes in OP-1 levels in a cell or fluid.

XI. Exemplary Screening Assay for Compounds which Alter OP-1 Gene Expression in Endogenous Cell Type Models.

OP-1 is expressed in a variety of different cell types, including renal, bone, lung, heart, uterine, cardiac and neural tissue. Candidate compounds can be identified which have a modulating effect on cells of one tissue type but not another, and/or wherein the effect is modulated in the different cells. The assay described below can be used to evaluate the effect of a candidate compound(s) in a particular cell type known to express OP-1 under physiological conditions.

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of OP-1 production includes culture supernatants or cell lysates, collected periodically and evaluated for OP-1 production by immunoblot analysis Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo OP-1 synthesis, some cultures are labeled according to conventional procedures with an $^{35}$S-methionine/$^{35}$S-cysteine mixture for 6–24 hours and then evaluated to OP-1 synthesis by conventional immunoprecipitation methods.

XII. Exemplary In vivo Animal Model for Testing Efficacy of Compounds to Modulate OP-1 Expression It previously has been demonstrated that OP1 can effect osteoporosis on the standard ovariectomized rat model, as indicated by the dose-response increase in alkaline phosphate and osteocalcin levels following injection with OP-1. The osteoporotic rat model provides an in vivo model for evaluating the efficacy of a candidate modulating compound. In order to determine the effect of a candidate morphogen stimulating agent on OP-1 production and, thereby, on bone production in vivo, alkaline phosphate and osteocalcin levels are measured under conditions which promote osteoporosis, e.g., wherein osteoporosis is induced by ovary removal in rats and in the presence and absence of a candidate modulating compound. A compound competent to enhance or induce endogenous OP-1 expression should result in increased osteocalcin and alkaline phosphate levels.

Forty Long-Evans rats (Charles River Laboratories, Wilmington) weighing about 200 g each are ovariectomized (OVX) using standard surgical procedures, and ten rats are sham operated. The ovariectomization of the rats produces an osteoporotic condition within the rats as a result of decreased estrogen production. Food and water are provided ad libitum. Eight days after ovariectomy, the rats, prepared as described above, are divided into three groups: (A) sham-operated rats; (B) ovariectomized rats receiving 1 ml of phosphate-buffered saline (PBS) i.v. in the tail vein; and (C) ovariectomized rats receiving various dose ranges of the candiate stimulating agent either by intravenous injection through the tail vein or direct administration to kidney tissue.

The effect of the candidate compound on in vivo bone formation can be determined by preparing sections of bone tissue from the ovariectomized rats. Each rat is injected with 5 mg of tetracycline, which will stain the new bone (visualized as a yellow color by fluorescence), on the 15th and 21st day of the study, and on day 22 the rats are sacrificed. The body weights, uterine weights, serum alkaline phosphate levels, serum calcium levels and serum osteocalcin levels then were determined for each rat. Bone sections are prepared and the distaance separating each tetracycline straining is measured to determine the amount of new bone growth. The levels of OP-1 in serum following injection of the candidate agent also can be monitered on a period basis using, for example, the immunoassay described in sections V and VII above.

V. Exemplary Determination of OP-1 Protein Production

Where OP-1 acts as the reporter gene, detection to the gene product readily can be assayed using antibodies specific to the protein and standard immunoassay testings. For example, OP-1 may be detected using a polyclonal antibody specific for OP-1 in an ELISA, as follows.

1 μg/100 μl of affinity-purified polyclonal rabbit IgG specific for OP-1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 μl aliquot of an appropriate dilution of each of the test samples of cell culture supernatant is added to each well in triplicate and incubated at 37° C. for 30 min. After incubation, 100 ul biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl streptavidin-alkaline (Southern Biotechnology Associates, Inc. Birmingham, Alabama, diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well incubated at room temperature for 15 min. Then, 50 μl amplifier (from the same amplification system kit) is added and incubated for another 15 min at room temperature. The reaction is stopped by the addition of 50 μl 0.3 M sulphuric acid. The OD at 490 nm of the solution in each well is recorded. To quantitate OP-1 in culture media, a OP-1 standard curve is performed in parallel with the test samples.

VI. Exemplary Production of OP-1 Polyclonal and Monoclonal Antibody

Polyclonal antibody for OP-1 protein may be prepared as follows. Each rabbit is given a primary immunization of 100 μg/500 μl E. coli produced OP-1 monomer (amino acids 328–431 in SEQ ID NO:5) in 0.1% SDS mixed with 500 ul Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 μg of antigen and bled (15 ml per bleed) at days seven and ten after boosting.

Monoclonal antibody specific for OP-1 protein may be prepared as follows. A mouse is given two injections of E. coli produced OP-1 monomer. The first injection contains 100 μg of OP-1 in complete Freund's adjuvant and is given subcutaneously. The second injection contains 50 μg of OP-1 in incomplete adjuvant and is given intraperitoneally. The mouse then receives a total of 230 μg of OP-1 (amino acids 307–431 in SEQ ID NO:5) in four intraperitoneal injections at various times over an eight month period. One week prior to fusion, both mice are boosted intraperitoneally with 100 μg of OP-1 (307–431) and 30 μg of the N-terminal peptide ($Ser_{293}$-Asn309g-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP-1-specific antibodies using OP-1 (307–431) as antigen. The cell fusion and monoclonal screening then are according to standard procedures well described in standard texts widely available in the art.

VII. Exemplary Process for Detecting OP-1 in Serum

Presented below is a sample protocol for identifying OP-1 in serum. Following this general methodology OP-1 may be detected in body fluids, including serum, and can be used in a protocol for evaluating the efficacy of an OP-1 modulating compound in vivo.

A monoclonal antibody raised against mammalian, recombinantly produced OP-1 using standard immunology techniques well described in the art and described generally in example VI., above, was immobilized by passing the antibody over an agarose-activated gel (e.g., Affi-Gel ™, from Bio-Rad Laboratories, Richmond, Calif., prepared following manufacturer's instructions) and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50)% acetonitrile/0.1% TFA gradient. Mature, recombinantly produced OP-1 homodimers elute between 20–22 minutes, and are used as a positive control. Fractions then were collected and tested for the presence of OP-1 by standard immunoblot using an OP-1 specific antibody. Using this method OP-1 readily was detected in human serum. See also, PCT/US92/07432 for a detailed description of the assay.

IX. Considerations for Formulations and Methods for Administering Therapeutic Agents Where the OP-1-modulating agent identified herein comprises part of a tissue or organ preservation solution, any commercially available preservation solution may be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell, (solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. Organ preservation solutions also may contain anticoagulants, energy sources such as glucose, fructose and other sugars, metabolites, heavy metal chelators, glycerol and other materials of high viscosity to enhance survival at low temperatures, free oxygen radical inhibiting agents and a pH indicator. A detailed description of preservation solutions and useful components may be found, for example, in U.S. Pat. No. 5,002,965.

Where the OP-1-modulating agent is to be provided to an individual, e.g., the donor prior to harvest, or the recipient prior to or concomitant with transplantation, the therapeutic agent may be provided by any suitable means, preferably directly (e.g., locally, as by injection to the tissue or organ locus) or systemically (e.g., parenterally or orally).

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations may include, for example, polyalkylene glycols such as polyethylene glycol, oils of vegetable original, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide and glycolide polymers and lactide/glycolide copolymers, may be useful excipients to control the release of the agent in vivo.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. Where the morphogen-stimulating agent is part of a preservation solution, the dosage likely will depend for example, on the size of the tissue or organ to be transplanted, the overall health status of the organ or tissue itself, the length of time between harvest and transplantation (e.g., the duration in storage), the frequency with which the preservation solution is changed, and the type of storage anticipated, e.g., low temperature. In general terms, preferred ranges include a concentration range between about 0.1 ng to 100 μg/kg per tissue or organ weight per day.

Where the therapeutic agent is to be administered to a donor or recipient, the preferred dosage of drug to be administered also is likely to depend on such variables as the type and extent of progression of the disease, the overall health status of the particular patient, the relative biological efficacy of the compound selected, the formulation of the compound excipients, and its route of administration. In general terms, a suitable compound of this invention may be provided in an aqueous physiological buffer solution containing about 0.001% to 10% w/v compound for parenteral administration. Typical dose ranges are from about 10 ng/kg to about 1 g/kg of body weight per day; and preferred dose range is from about 0.1 μg/kg to 100 mg/kg of body weight per day.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An isolated nucleic acid having a nucleotide sequence comprising nucleotides 1 to 3317 of Seq. ID No. 1.

2. An isolated nucleic acid having a nucleotide sequence comprising nucleotides 1 to 1871 of Seq. ID No. 2.

3. An isolated nucleic acid comprising a reporter gene in operative association with a single nucleic acid fragment of an osteogenic protein-1 (OP-1) specific upstream non-coding sequence, wherein said nucleic acid fragment consists of nucleotides 3170 to 3317, 3020 to 3317, 2790 to 3317, 2548 to 3317, 2300 to 3317, 1300 to 3317, 2548 to 2790, 1549 to 2790, or 1 to 2790 of SEQ ID NO: 1,
wherein said isolated nucleic acid comprises not more than one nucleic acid fragment of said OP-1 upstream sequence, and wherein said nucleic acid fragment is operative to regulate expression of said reporter gene.

4. The nucleic acid of claim 3 wherein said nucleic acid fragment consists of nucleotides 3170 to 3317, 3020to 3317, 2790to 3317, or 2548 to 3317 of SEQ ID NO: 1.

5. The nucleic acid of claim 3 wherein said nucleic acid fragment consists of nucleotides 2300 to 3317, 1300 to 3317, 2548 to 2790, 1549 to 2790, or 1 to 2790 of SEQ ID NO: 1.

6. The nucleic acid of claim 3 wherein said nucleic ad fragment comprises at least one Wt-1/Egr consensus binding element.

7. The nucleic acid of claim 3 wherein said nucleic acid fragment comprises between one and six Wt-1/Egr binding elements.

8. The nucleic acid of claim 3 wherein said nucleic acid fragment comprises at least part of an Fushi-tarazu protein binding element.

9. The nucleic acid of claim 3 wherein said nucleic acid fragment comprises a steroid responsive element.

10. A kit for identifying a candidate molecule capable of modulating osteogenic protein-1 (OP-1) expression in a cell, the kit comprising:
    (a) a receptacle containing an isolated nucleic acid of claim 3; and
    (b) means for detecting expression of said reporter gene following exposure of a said candidate molecule to a cell containing said nucleic acid.

11. The kit of claim 10 wherein said reporter gene comprises an OP-1 DNA sequence.

12. The kit of claim 10 wherein said reporter gene is in operative association with a single nucleic acid fragment consisting of nucleotides 3170 to 3317, 3020to 3317, 2790to 3317,or 2548to 3317of SEQ ID NO: 1.

13. The kit of claim 10 wherein said reporter gene is in operative association with a single nucleic acid fragment consisting of nucleotides 2300 to 3317, 1300 to 3317, 2548 to 2790, 1549 to 2790, or 1 to 2790 of SEQ ID NO: 1.

14. A cell transfected with the nucleic acid of any of claims 3, 4, 5, 6, 7 or 8.

15. The transfected cell of claim 14 wherein at least part of said nucleic acid is operatively integrated into the cellular genome.

16. The transfected cell of claim 15 wherein the genome of said cell has an OP-1 gene locus and at least part of said transfected nucleic acid is operatively integrated into said genome at said OP-1 locus.

17. The transfected cell of claim 14 wherein said cell expresses endogenous OP-1.

18. The transfected cell of claim 17 wherein said cell is an epithelial cell.

19. The transfected cell of claim 17 wherein said cell is of urogenital, liver, bone, cardiac, lung, or nerve cell origin.

20. A method for screening a candidate compound for the ability to modulate expression of osteogenic protein (OP-1), said method comprising the steps of:
    (a) incubating a said candidate compound with a cell transfected with an isolated nucleic acid of claim 3;
    (b) measuring the level of said reporter gene expressed in said cell; and
    (c) comparing said level with that of said reporter gene expressed in said cell in the absence of said candidate compound, wherein an increase in reporter gene expression level is indicative of said candidate's ability to increase OP-1 expression in vivo, and a decrease in reporter gene expression level is indicative of the candidate's ability to inhibit OP-1 expression in vivo.

21. The method of claim 20 wherein said reporter gene is in operative association with a single nucleic acid fragment consisting of nucleotides 3170 to 3317, 3020 to 3317, 2790 to 3317, or 2548 to 3317 of SEQ ID NO: 1.

22. The method of claim 20 wherein said reporter gene is in operative association with a single nucleic acid fragment consisting of nucleotides 2300 to 3317, 1300 to 3317, 2548 to 2790, 1549 to 2790, or 1 to 2790 of SEQ ID NO: 1.

23. The method of claim 20 wherein said isolated nucleic acid further comprises part or all of a nucleotide sequence encoding an OP-1 pro protein in operative association with said reporter gene.

24. The method of claim 20 wherein said cell is an epithelial cell.

25. The method of claim 20 wherein said cell is of urogenital, liver, bone, cardiac, lung, or nerve cell origin.

26. An isolated nucleic acid comprising a reporter gene in operative association with:
    a) a nucleic acid fragment of an osteogenic protein-1 (OP-1) specific upstream non-coding sequence, wherein said nucleic acid fragment consists of nucleotides 2151 to 2297, 2001 to 2297, 1788 to 2297, 1549 to 2297, 800 to 2297, 1 to 2297, 1549 to 1788, 800 to 1788, or I to 1788 of SEQ ID NO: 2; or
    b) a variant of a nucleic acid fragment of a) which hybridizes with a nucleic acid complementary to the nucleic acid fragment of a) under conditions of hybridization in 40% formamide, 5× SSPE, 5 × Denhardt's solution, and 0.1% SDS at 37° centigrade, followed by washing in 0.1× SSPE, and 0.1% SDS at 50° centigrade, wherein the nucleic acid fragment of a) or b) is operative to regulate expression of said reporter gene.

27. The nucleic acid of claim 26 wherein said reporter gene is, in operative association with:
   a) a nucleic acid fragment consisting of nucleotides 2151 to 2297, 2001 to 2297, 1788 to 2297, or 1549 to 2297 of SEQ ID NO: 2; or
   b) a variant of a nucleic acid fragment of a) which hybridizes with a nucleic acid complementary to the nucleic acid fragment of a) under conditions of hybridization in 40% formamide, 5× SSPE, 5× Denhardt's solution, and 0.1% SDS at 37° centigrade, followed by washing in 0.1 × SSPE, and 0.1% SDS at 50° centigrade.

28. The nucleic acid of claim 26 wherein said reporter gene is in operative association with:
   a) a nucleic acid fragment consisting of nucleotides 800 to 2297, 1 to 2297, 1549 to 1788, 800 to 1788, or 1 to 1788 of SEQ ID NO: 2; or
   b) a variant of a nucleic acid fragment of a) which hybridizes with a nucleic acid complementary to the nucleic acid fragment of a) under conditions of hybridization in 40% formamide, 5 × SSPE, 5 × Denhaidt's solution, and 0.1% SDS at 37° centigrade, followed by washing in 0.1 × SSPE, and 0.1% SDS at 50° centigrade.

29. A kit for identifying a candidate molecule capable of modulating osteogenic protein-1 (OP-1) expression in a cell, the kit comprising:
   (a) a receptacle containing an isolated nucleic acid of claim 26, and
   (b) means for detecting expression of said reporter gene following exposure of a said candidate molecule to a cell containing said nucleic acid.

30. The kit of claim 29 wherein said reporter gene comprises an OP-1 DNA sequence.

31. The kit of claim 29 wherein said reporter gene is in operative association with
   a) a nucleic acid fragment consisting of nucleotides 2151 to 2297, 2001 to 2297, 1788 to 2297, or 1549 to 2297 of SEQ ID NO: 2; or
   b) a variant of a nucleic acid fragment of a) which hybridizes with a nucleic acid complementary to the nucleic acid fragment of a) under conditions of hybridization in 40% formamide, 5× SSPE, 5× Denhardt's solution, and 0.1% SDS at 37° centigrade, followed by washing in 0.1× SSPE, and 0.1% SDS at 50° centigrade.

32. The kit of claim 29 wherein said reporter gene is in operative association with:
   a) a nucleic acid fragment consisting of nucleotides 800 to 2297, 1 to 2297, 1549 to 1788, 800 to 1788, or 1 to 1788 of SEQ ID NO: 2; or
   b) a variant of a nucleic acid fragment of a) which hybridizes with a nucleic acid complementary to the nucleic acid fragment of a) under conditions of hybridization in 40% formarnide, 5× SSPE, 5× Denhardt's solution, and 0.1% SDS at 37° centigrade, followed by washing in 0.1 × SSPE, and 0.1% SDS at 50° centigrade.

33. A method for screening a candidate compound for the ability to modulate expression of osteogenic protein (OP-1), said method comprising the steps of:

(a) incubating a said candidate compound with a cell transfected with an isolated nucleic acid of claim 26;

(b) measuring the level of said reporter gene expressed in said cell; and (c) comparing said level with that of said reporter gene expressed in said cell in the absence of said candidate compound, wherein an increase in reporter gene expression level is indicative of said candidate's ability to increase OP-1 expression in vivo, and a decrease in reporter gene expression level is indicative of the candidate's ability to inhibit OP-1 expression in vivo.

34. The nucleic acid of claim 3, 4, 5, 26, 27, or 28 further comprising part or all of a nucleotide sequence encoding an OP-1 pro protein in operative association with said reporter gene.

35. A vector comprising the nucleic acid sequence of claim 1, 3, 4, 5, 26, 27, or 28.

36. A cell transfected with an isolated nucleic acid, said nucleic acid comprising a reporter gene in operative association with a first DNA sequence, wherein said first DNA sequence is:
   a) a single nucleic acid fragment of an osteogenic protein-1 (OP-1) specific upstream non-coding sequence, wherein said nucleic acid fragment consists of nucleotides 2548 to 3317 or 2548 to :2790 of SEQ ID NO: 1; or
   b) a nucleic acid fragment of an osteogenic protein-1 (OP-1) specific upstream non-coding sequence, wherein said nucleic acid fragment consists of nucleotides 1549 to 2297, or 1549 to 1788 of SEQ ID NO: 2; or
   c) a variant of a nucleic acid fragment of b) which hybridizes with a nucleic acid complementary to the nucleic acid fragment of b) under conditions of hybridization in 40% formamide, 5× SSPE, 5× Denhardt's solution, and 0.1% SDS at 37° centigrade, followed by washing in 0.1× SSPE, and 0.1% SDS at 50° centigrade; and
   a second DNA sequence comprising a sequence which interacts with a DNA binding molecule and affects expression of said reporter gene,
   wherein said isolated nucleic acid comprises not more than one nucleic acid fragment of a).

37. The cell of claim 36 wherein said second DNA sequence comprises at least one Wt-1/Egr-1 consensus element SEQ ID NO: 4.

38. The cell of claim 37 wherein said second DNA sequence comprises between one and six Wt-1/Egr-1 consensus elements SEQ ID NO: 4.

39. The cell of claim 37 wherein said second DNA sequence comprises at least six Wt-1/Egr-1 consensus elements SEQ ID NO: 4.

40. The cell of claim 36 wherein said second DNA sequence is selected from the group of sequences consisting of a TCC element, a Fushi-tarazu protein binding element and a steroid responsive element.

41. The cell of claim 36 further comprising a third DNA sequence in operative association with said reporter gene, said third DNA sequence being independently selected from the group of sequences consisting of a TCC element, a Fushi-tarazu protein binding element and a steroid responsive element.

42. A method for screening a candidate compound for the ability to modulate expression of OP-1, said method comprising the steps of:

(a) incubating a said candidate compound with a cell according to claim 36, 37, 40 or 41;

(b) measuring the level of reporter gene expressed in said cell; and (c) comparing said level with that of said reporter gene expressed in said cell in the absence of said candidate compound, wherein an increase in reporter gene expression level is indicative of said candidate's ability to increase OP-1expression in vivo, and a decrease in reporter gene expression level is indicative of the candidate's ability to inhibit OP-1 expression in vivo.

43. The method of claim 42 wherein said cell is an epithelial cell.

44. The method of claim 42 wherein said cell is of urogenital, liver, bone, cardiac, lung, or nerve cell origin.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 17415 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
    (A) ORGANISM: homo sapiens (xi) SEQUENCE DESCRIPTION: SEQ ID NO:1:

```
TCAACCGGTC TCTTTAGGTT TTGGCTGTGC TTATTACTAT TCATTCAACA GGTACTAATT      60

GAGCACCTGC TGTGTGCCAG GCTCAGAATA GGCTCAGGTG AGATGCACAA AGAAGGGTAA     120

ACTAGAATCC TTGCTTAGAC ACTGACGGAT CAGTTGTTTC ATATGTAAAT TGTAGCACCA     180

AGACCTGCTG CCCCTGCCCC CAGCCTCACC TGCTTGTGAA GATCCCTCCA AAAGATTTGA     240

GAGTAGATAA AAAGCAGAGA CTACTACTGA AGAACAGGGC TGCTTTGGCT CCTTATTATT     300

TCAGACTTTG GAAGAAAATG ACCTCCTTTT TCTCTACTGG CACTGAGTGC ATAGCTGACC     360

TAGCAAGCCA GGCCTGGAGG GCGTGTGCAG GGCTGGGGAC CGAGCCTGGT TTCTGTTCCC     420

TGCTCTGCAG CTCAAGCACT TGCTGTTCCT CCACCTGGGA TGCCTTTCCC TGGAAAAGCC     480

TGTCTCTTTC TTGTCTTTCA GGACTCAGGT CAGTGGCATC TCCTCCAAAA ACTCCCCTTC     540

CCACCCTCCA TCACCTCACC CTGTTTATCT GCGCCCCCGC CCCCACTGCC TGTCACTTAT     600

TGCAGGCTGA AGTGACCCAG GCTCTCCAGT TGTACACTCT CAGATGGACC CTGGACGACT     660

GTGGCACTCC TGCAATTTCC CCAGTCTCCC TGGGGTAGGA TTCCTGCTTG CCAGGATGCC     720

CACCTTTCCT TCTCCCTCCT GCATGTCCTC CTCTGCCTGG CTTCTGAATT GTTTCCAGAG     780

AGAGTGATAG ACAAGATCTG CCTCTCCTTC AGTCCCTGAA TCTTATTTAA GGCTCTTGCT     840

TTGCTTCCCT GGCCTGGAGG CGGCTCCTTG ATGGAGTCTG CCATGTGGGT TCGCTCATGG     900

CCATGTCTTC CTGCCCAGCA TGGTGCTTGG CCCTGGGACT GGCCACATAA TATCTGGGCC     960

AGGTGCAAAA TTAGTACGGG GCAGGGGGTA CTTTGTTCAT AGGTGATTCA GAACCACATA    1020

TGGTGACCTC AGAGTAGGAA ACCAAGTGTG GGGCCCTTAA GAGCTGGGGG GCCCTGTACG    1080

ACTGTCCAGG TTGCAGGCCC CACAGCTCGC CTCCTGATAT CCTGTGCTCC ATGCTTGTCT    1140

GTTGAAGGAA GGAGTGAATG GATGAAGAGC AGGTGGTGGG GGGTGGTTTG AGGGCCTTGC    1200

TGGTGGGTGG GTAGAGGCCC CTCCCTGGCA TGGGGCTCAA GACCTGTTCC ATCCCACAGC    1260

CTGGGGCTGT GTGTAAATGG CCAGGACCTG CAGGCTGGCA TTTTTCTGCT CCTTGCCTGG    1320

CTCTGGCTCC CCTTTCTCCA CCCATGTGGC CCCTCAGGCT GCCATCTAGT CCAAAAGTCC    1380

CAAGGGAGAC CCAGAGGCCA CTTGGCAAAC TACTTCTGCT CCAGAAAACT GTAGAAGACC    1440

ATAATTCTCT TCCCCAGCTC TCCTGCTCCA GGAAGGACAG CCCCAAAGTG AGGCTTAGCA    1500

GAGCCCCTCC CAGACAAGCG CCCCCGCTTC CCCAACCTCA GCCCTTCCCA GTTCATCCCA    1560

AAGGCCCTCT GGGGACCCAC TCTCTCACCC AGCCCCAGGA GGGAAGGAGA CAGGATGAAC    1620

TTTTACCCCG CTGCCCTCAC TGCCACTCTG GGTGCAGTAA TTCCCTTGAG ATCCCACACC    1680

GGCAGAGGGA CCGGTGGGTT CTGAGTGGTC TGGGGACTCC CTGTGACAGC GTGCATGGCT    1740

CGGTATTGAT TGAGGGATGA ATGGATGAGG AGAGACAGGA GAGGAGGCCG ATGGGGAGGT    1800

CTCAGGCACA GACCCTTGGA GGGGAAGAGG ATGTGAAGAC CAGCGGCTGG CTCCCCAGGC    1860

ACTGCCACGA GGAGGGCTGA TGGGAAGCCC TAGTGGTGGG GCTGGGGTGT CTGGTCTCAG    1920

GCTGAGGGGT GGCTGGAAAG ATACAGGGCC CCGAAGAGGA GGAGGTGGGA AGAACCCCCC    1980

CAGCTCACAC GCAGTTCACT TATTCACTCA ACAAATCGTG ACTGCGCACG TACAGTGGCT    2040

ACCAGGCGCT GGGTTCAAGG CACTGCGGGT ACCAGAGGTG CGGAGAAGAT CGCTGATCCG    2100

GGCCCCAGTG CTCTGGGTGT CTAGCGGGGG TAAGAAGGCA ATAAAGAAGG CACGGAGTAA    2160

CTCAAACAGC AATTCCAGAC AGCAAGAGAA ACTACAGGAA AGAAAACAAA CGTGCGAGGG    2220
```

```
GCGAGGCGAG GAAACAACCT CAGCTTGGCA GGTCTTGGAG GTCTCTGGGA GGAGAAAGCA      2280

GCGTCTGATG GGGGCGGGAG GTGGTGAGTG GGGAGAGGTC CAGGCGGAGG GAATGGCGAG      2340

CGAGAGACAG GCTGGCAACG GCTTCAGGGA GGCGCGGAGG GGTCAGCGTG GCTGGCTTAA      2400

AAGGATACAT GGGACTAGGG GCAAGACCGG CTCAAGGTCA CCGCTTCCAG GACCTTCTAT      2460

TTCCGCGCCA CCTCCGCGCT CCCCCAACTT TTCCCACCGC GGTCCGCAGC CCACCCGTCC      2520

TGCTCGGGCC GCCTTCCTGG TCCGGACCGC GAGTGCCGAG AGGGCAGGGC CGGCTCCGAT      2580

TCCTCCAGCC GCATCCCCGC GACGTCCCGC CAGGCTCTAG GCACCCCGTG GCACTCAGT      2640

AAACATTTGT CGAGCGCTCT AGAGGGAATG AATGAACCCA CTGGGCACAG CTGGGGGGAG      2700

GGCGGGGCCG AGGGCAGGTG GGAGGCCGCC GGCGCGGGAG GGGCCCCTCG AAGCCCGTCC      2760

TCCTCCTCCT CCTCCTCCGC CCAGGCCCCA GCGCGTACCA CTCTGGCGCT CCCGAGGCGG      2820

CCTCTTGTGC GATCCAGGGC GCACAAGGCT GGGAGAGCGC CCCGGGGCCC CTGCTATCCG      2880

CGCCGGAGGT TGGAAGAGGG TGGGTTGCCG CCGCCCGAGG GCGAGAGCGC CAGAGGAGCG      2940

GGAAGAAGGA GCGCTCGCCC GCCCGCCTGC CTCCTCGCTG CCTCCCCGGC GTTGGCTCTC      3000

TGGACTCCTA GGCTTGCTGG CTGCTCCTCC CACCCGCGCC CGCCTCCTCA CTCGCCTTTT      3060

CGTTCGCCGG GGCTGCTTTC CAAGCCCTGC GGTGCGCCCG GGCGAGTGCG GGGCGAGGGG      3120

CCCGGGGCCA GCACCGAGCA GGGGGCGGGG GTCCGGGCAG AGCGCGGCCG GCCGGGGAGG      3180

GGCCATGTCT GGCGCGGGCG CAGCGGGGCC CGTCTGCAGC AAGTGACCGA GCGGCGCGAC      3240

GGCCGCCTGC CCCCTCTGCC ACCTGGGGCG GTGCGGGCCC GGAGCCCGGA GCCCGGGTAG      3300

CGCGTAGAGC CGGCGCGATG CACGTGCGCT CACTGCGAGC TGCGGCGCCG CACAGCTTCG      3360

TGGCGCTCTG GCACCCCTG TTCCTGCTGC GCTCCGCCCT GGCCGACTTC AGCCTGGACA      3420

ACGAGGTGCA CTCGAGCTTC ATCCACCGGC GCCTCCGCAG CCAGGAGCGG CGGGAGATGC      3480

AGCGCGAGAT CCTCTCCATT TTGGGCTTGC CCCACCGCCC GCGCCCGCAC CTCCAGGGCA      3540

AGCACAACTC GGCACCCATG TTCATGCTGG ACCTGTACAA CGCCATGGCG GTGGAGGAGG      3600

GCGGCGGGCC CGGCGGCCAG GGCTTCTCCT ACCCCTACAA GGCCGTCTTC AGTACCCAGG      3660

GCCCCCCTCT GGCCAGCCTG CAAGATAGCC ATTTCCTCAC CGACGCCGAC ATGGTCATGA      3720

GCTTCGTCAA CCTCGGTGAG TAAGGGCAGG CGAGGGTACG CCGTCTCCTT TCGGGGCAC      3780

TTTGAGACTG GGAGGGAGGG AGCCGCTTCT TCTATGCAGC CCGCCCAGCT TTCCGCTCCT      3840

GGCTGAAATC GCAGTGCCTG CCCGAGGGTC TCCCACCCAC AGCCCTATGA CTCCCAAGCT      3900

GTGTGCGCCC CCAGGTCGGG CCGCTGGGTC GGTGAGCCTG TAGGGGTTAC TGGGAAGGAG      3960

GGATCCTCCG AAGTCCCCTC CATGTTACGC CGCCGGCCGC ATCTCTGGGG CTGGAGGCAA      4020

GGGCGTTCAA AGCGCGGGGC TCGGTCATGT GAGCTGTCCC GGGCCGGCGC CGGTCCGTGA      4080

CCTGGATGTA AAGGGCCCTT CCCGGCGAGG CTGCCTTGCC GCCCTTCCTG GCCCCTCTC      4140

AGCCCTGCCT GGCTCTGGCA TCGCGGCCGT CGCACCCCCT TACCCTCCCT GTCAAGCCCT      4200

ACCTGTCCCC TCGTGGTGCG CCCGCCTTAG GCTACCGGCC GCTCCGAGCC TTGGGGCCCC      4260

TCTCCGGGCG CCGATGCCCC ATTCTCTCTT GGCTGGAGCT GGGGAAGAAA CGGTGCCATT      4320

GCTAATTTTC TTTGTTTTCT TTCTTTGTTT ATTTTTTTCT TTTTTTCTTTT TTTTTCTTTT      4380

CTTTTCTTTT CTTTTTTTTT TTTTTGAGA CGGAGTTTCA CTCTTGCTCG CCCAGACTGG      4440

AGTGCAATGG CGCGATCTCT GCTCACCGCA ACCTCTGCCT CCCGGGTTCA AGCGATTCTC      4500

GTGCCTCAGC CTCCCGAGTA GCTGGGATTA CAGGCATGCG CACCATGCCT GGCTAATTTT      4560

GTATTTTAGT AGAGACAGGG TTTCTCCATG TTAGGCAGGC TGGTCTCGAA CTCCCGATCT      4620
```

-continued

```
CAGGTGATCC TCCCGCCTCA GCCTCCCAAA GTGGTGCTGG GATTACAGGC GTGAAGCTGT    4680
GCCCTGCCGC TAGTCTTCTA TTTTAAGTAT TTAGTGGTAG GTCCCGGGCC GGCAGAATCT    4740
ATTTTCAGCA TTTACCACGT GTGGCGCGCA AACCACAGGT TTTGGCGATT GGGTTGCGCG    4800
GGATCTCAGA GCTGACGACC GCGGGGGCCT GGGGGTCCCG GTTTCCGACT GGAGCCGCGA    4860
CGACCCCGGC GACGGCAGCC TGGGGCTGCA GCCGAGGGCC GGGGAGCTCC CCCTCCATAT    4920
GTGCGCGCAC ATTCTCCAGA CTTGCTCAAA CTAACCCCCC GGAGCAGCGC ACGGGCTGGG    4980
ACTGATGATC AAATATTTGG TTTCCGAGAT AACACACCCC GATAGCGCTG TTTCCTGAGC    5040
CGCTTTCATT CTACTTGTGT AACTTGCTGC GAAAACCCGA ACCAAGTCAA GACAGCAAAC    5100
TCACGCCCAC GGGCCTGTGT CAACATGGAA ATAATGATAC TGAAGCCCCA CGCTGGGCAC    5160
CTGGGGCGTG GACTGGGGGC GCGGGGGAAG CGCAGATCCG CCTTCATGCT TCCCCTCCTC    5220
CTGATAAGGT CCCTGGAGTT CCCGGGAGCC ATTGTCTGTA CTTAATAATA ACTAAATCCA    5280
ACTAGTGAAC CAAGCTTCAG CGAGGCAAGG GGAGGGAGGT TTAGATGCCA AAATTACCTT    5340
CAAAAAAGTT TAAATTATAC TAAGCAGCCA GTTAAGAAGG AAGCAGCAAT ATATGACCTG    5400
ATTTAGAACC ATCTCCAAGA TGTATGAGGT GGAAAGAAGC AAGGTGCAGA TGAGTGGGCT    5460
GCATGTGTGC TTGTATATCA TCGTGTCCTC CTGGAGGAAG ACACCAGGAA CTGGAGAGAG    5520
ATTTACTGG AGGGGTATAT GGCGGGGGCA TAGCTGGGGC TTACGGAGTG GGAGGTGGGG    5580
TCTGATTTTT CGTCGTCTGC ACTTCTGTAT TTGTGATTTT TTTAAAACAA TGTGTATTTA    5640
TTAACTATAC CAAAAAATAA AGGAAAATTC CAAATACATA CATATAAATA ATGAACCGCA    5700
GAGCTCTGTC GCCCTCCTGA AGCCTGGGGT TAGCCAGGGC CCTTTCTCTG GTGGGGGATT    5760
TATAGCATCT TCCCTTCTGT TGGGTACCCC GGACTCCCAC TGAATGTGCA GGTCCCAGTG    5820
GCTGCCTTCA GAGCCTGGCT GGAATCATTA AAAAGGTATT TGTAATCTCT GGCTTCTGCA    5880
GAAGGCCCTG CAAACCAAGA GCAAAAAAGC CCCCAGTGCT TATGGGCCGG CAGTGTGGGC    5940
TAGGCCCGGG GCTCCCTGTC CCCAAGAGAA AGACCAGGTT GCTCGGAGGG TGCCTCTGGG    6000
AACTTTGGTG CGGGCTATTT GCTCCCCCCA TGGCGGCAGG AGCAAGCTGG GACTTGTTTG    6060
GGAAGGCCAC AGCTGGGTGG TTTTCCTCCT CTGGCTGTAC ATACACCTTT CAATCCATTT    6120
CTTTCATCTT GAAAGGACAA AGACCGGCTT GTCTGAGCCT CTTAATCAGT CAGGCTGGCT    6180
TTGGGCTTTG GGGACCCTGA CTTTCTCAGG TCTAGCTTTC TGGGACATCA CTCCAAATTA    6240
GATGGCAGAG TGGCTTTTAA CAGAGCGCAC TGACCTTGTT TTCTTTCTCT CTCTGTCCCT    6300
AAACTCGAGG TCATTAGTTA GGTGAAGACC TGGGCTGCAG TTTGGCGAGA CACTTCCTGT    6360
AGATGCTTCT AATGTTGGCC TTTAATTTCT GCTAAGCAGC AGCACACAAA TAAATGGCCT    6420
GTCCCTTCTA TCCTGTTGTA GCTTGGAATT TCTCCATAGG AGGGACTTGG GGGTGGCAGT    6480
AGGGTTGGAG AGGGTTGGGG GGAGGTGTAG GAGACTTGTC TGGCCACTGA GTTTGCTGAG    6540
AAAGTACTGC TATAGTGTTT TTCCTTGGAT TGCAAATCAT GTTGATCTGA ACTGCTGATT    6600
TGAAGTGGAT TGAGAGGATG GAACAATAGA AGGAGGATAT GGCTCAGGAC AGTCAAGTAC    6660
TGGAAGAGGG AAAGGTACAA AGAGGTGTTG GCACTGAATG ACCCTGAACA GGGCTGCCCT    6720
GGAAATATCA GAGGTGAGTG ACAAAGAGAA CTCTAGTCGA AGGTCTGGAA GTCAATTATT    6780
GTCTCCAGCT TTTGTCCCAC CCTAAGGGAT GGAGCATGAA CTTCATGCAT GTAACATCCC    6840
TCCAGGAGCG CTGAGGTTCT GGGAATTCCC AGTGCTGGCT ACCATGCCAT TCTTTTCTCA    6900
TTCACTCAAG AGCGTATTGG GATATGCGTG CATGAAAGCA ATGTAATTAT GGGCACAACC    6960
TCAAAACCTG CTCTAATTTT TTTTTTTTTT GGAGATGGAG TCTCGCTCCA TCACCCAGGC    7020
```

```
TGGAGTGCAA TGGCGCGATC TCAGCTCACT GCAAGCTCAG ACCTCCAGGG TTCACACCAT     7080

TCTCCTGCCT CAGCCTCCCG AGTAGCTGGG AATACAGGCG CCCGCACCAT GCGCGGCTAA     7140

TTTTTTTGTA TTTTTAGTAG AGACGGGGTT TCACTGTGTT AGCCAGGATG GTCTCGATCT     7200

CCTGACCTCG TGATCCACCC GCCTCGGCCT CCCAAAGTTC TGGGATTACA GGCGTGACAG     7260

CCGTGCCCGG AATCTGCTCT AATTTTTTAA AGATATCATT TGCAAACTTT GGCACTTGA      7320

GTCACTCAGT AAGATATTAT TTACAACCCC ACCATAGATT CAAACCTCTG TCCTAGAATG     7380

TTGTCGAGTT AGGCATCTGG CTTGCAGCAA CAGCTGGCTT TCCTGTCTAT GCTGTCTCCT     7440

TCCAGGGAGG ATGTTTCACC CTTCATATTG AGGAAATGGG CACAGAGAAC CCATTTCTCT     7500

TACTCATCAT GTAACTTCAG TGGGATGGTC AGATCTATCT TTAACCTGGC CACTCTTCCA     7560

CAAGCTCACA CTGACTCCAG CAAGATCTTA AACTAGAAGG CAGGAGTTCA ATCCTAGCT      7620

GGTGCAGTGG CCAAATCTCG GCTCACAGCA CCTTCTGCCT CCTGGGCTCA AGCGATCCTC     7680

TGACCTCAGT CTCCCAAGTA GCTGGGACCA TAGGCATGCA CCACTATGCC TGGCTAATTT     7740

TTGTATTTTT GTAATTTTTT GTAGAGACAG AGTTTCACCA TGTTGCCCAG CCCAGTCTTG     7800

AACTCCTGGA CTCAAGCAAT CTTCCCACCT TTGCCTACCA GAGTGCCGGG ATTACAGGTG     7860

TGAGCCATCA TGCTAGTTGC GCACAGTTGG GCGAAACTGA CAGATGAGAA AGCAGAACCT     7920

CGTGAGTCCA CTCAGTAAGA GACTCCCTAC TTTCTTTCTG AGTCTTTGTT TCTCATCAAT     7980

TGAATGGCAA TAAACAACTT GGTGGCCCAA GAGTTGATGA CAACAGTCCT ATAAGATTAT     8040

ACATGTAAAA GAAACAGAGT ATTCTACAAA TATCAGTTAT TGATAGTTCA ATAGGCAACC     8100

TGACATTACC TTTTCTTGGA ACTTGATGAA CAACTCAGAA ACTCATTAAT ATCAAACCCA     8160

ATGGTGAGCA CTTGGTCTTT ATTTATGGCT GTAAGAGAAG AAATTGAATT AACTCTATGT     8220

AAATGCCAAC TAAGAACATC GAAGTCTGAA ATCAACAGTT TTCCTCGCTC ATACGACACA     8280

CCCAAACTCA AGCAGTGGTT CCAAGCCCCT TTGGAAAATA CCATGGGCTA ACGACTTTAA     8340

AAGCTTAGAA GTGAATTCTA CTTACTTATT ACTAAAAGT GGTTCTCAAA CTTCAAGGTG      8400

AATCAAAATC ATCTGTAGAG CTTGTTAAAA CACAGGTTGC TGGTCCACCC CAAGAGTGTC     8460

TTGAGTCAGT AGGTCTCAAG TAGGGCTCAA GAATATGCAT TTCTAATGAG CTCCAGGTGA     8520

GTCTAAGTGT TAGTCGTCGG TCTTGGGACC ACAACTTTGG GAACAATTGA TTTAGAAGAA     8580

CTCAAAGATC AGAAAGGGGT GGAATATTTT TAAAATTGTG GTAAAATACG CATAAACAGA     8640

AAAGGTACAA TTTTAACCAC TTAGAGAGAG GTGGGATCTA AGAACAGAAA TTGTTATGCC     8700

ATCAAAGGTG AGTTCAGATA AGCATTATTA AATGGTATCT ATGGATAAAC TTCAGGGGCC     8760

CTGTGGAGCA ACCCAATGCT GGGATGGGGT CCAGGTGTGC TATGGTTTGG ATGTGGTTTG     8820

TCCCTACAAA AACTCATGTT GAAATTTAAT TGCCAGTGTA ACATTATTGA GAGGTTATGG     8880

ACTTTTAAGA GGCATTTGGG TCATGAGGGA TCCACCTTCA GGGATTAGTG CAGTCTCCAG     8940

GGAGTGAGTG AGTTCCCATT CTAGTGGGAC TGGATTAGTT ACCATACAGT GGTTGTTATA     9000

AAGTGAGGCT GCTTCTGGTG TTTTATCTGT TTGCAGGCAC TTCCTTCCCC TTCCACTTCT     9060

CTGCCAGGTT AGGATGCAGC ATGAGGCCCT CACCAGAAGC TGACCAGATG TGGCTGCCTG     9120

ATCTTGAACT TCCCAGTCCC CAGAACCATG AGCTAAATAA ACCTTTTTTC TCTATAAATT     9180

ACGCAGTCTA GAGTATTCTA TTATAGCAAC ACAAGACAGA CTAAGACACA GTGGTAGAAA     9240

GAACACTACT GACTTCTCCC ATACTCTGGC CTATGGACAA GAGTGACAGA CAGACAAGAG     9300

TGAATATCAG GGCCCTCAGG CACATTCCTC TCTGCCCCTT CCTCCCTTCT TGCAGAGTCT     9360

CCAGTGACTG CCAGCTAATG CTATCATAGA CCCCACCTTT CCCCTGACTT GATTGGACCA     9420
```

```
GAAGCAGCCT CCTGATCCAT GGCCAACAAT CAGATTCACT TTCAAGAATT TGAACTAAGA    9480

GACACTAGGA AGATGGCCCT TGAGCTGTGA GTCCTACACT TGAAAGTTCT TAGCATCTTG    9540

GTCAGGTACC CACCAGGGCC ATGTGCAAAC TGAGATAATG GGGACATGGA ACAAGGGTAA    9600

GTGGAGAGGG CTGGCTGGAG AGAGACGGGC AGAGGAAAGC CCTGCCAAGA GGAGCAGAGA    9660

TGAGAGACCT TGGAGGGAGA GGTAATAAAA GGAGGCAAAG ATGATTTTCC ATGCTTACAA    9720

CTCACAGCTG AGGCCTAACT ATCTTTATGT CCATAAGAGG CATCCTTGTG TCGAACCTCT    9780

CCTCTTTCTT GGGTCAATGG GGATGGTTG CAAGGGACCA TCAGTAGGAA GGCATAGTAC    9840

ACTAACCCAG TCTGGGGTGG GCTTTTAGAC TAGTCTTCCT CCCATGCTCC TCCTCCCATT    9900

GGAACCCCGG ACTTTCAAGA CTGCTACCTA GCACACCAGT GCACCAGATG TCACTCAAAA    9960

CCTCTTCAGC AATGGCCCAC TCACCTTCAA AAAGGCTGAA GAGCAGACTG GCTGGGTTCT   10020

TCATGGTGGA GGGGCAGTCT GGGAGGTTTT AAGGTTGAAG ATGAAAACTT TCACTTTTGG   10080

CTCAATGGTC TGAAAAAGAG AAGGACCAGC AAGTGAACTG AAGCCTCCTG GAAAGCATCT   10140

TGATAACAGG GGCAGAGTTT CAAGATGAGA AGCTGTGGCA CTTACTCTGG CTTTGGAAAT   10200

GACCTCTAAG TATCTCAGTT AATTAAAGGA GTCAAACTCT AGACTCGAAG GAGAAGATCT   10260

ACAATTTTCA ATAACATAGT CTACCCTCCC CTCCTTCCCC CACCTTCACC TCTTCTTTCA   10320

TCACAGGCTT ACAGGGCACC TCTTAGAGCC AGGCACGGTG TTGGGATCAG GAACAAGGCC   10380

ACTGCTCACA TCCAGAGCCT GTGCTACTTA AGAAGCTTCC AGGACCTCTT GGATGGCTGT   10440

GGTTAGTGCC CTACTTTTCC CAGCAGGTTG GATGCAGAAT CATGCTCTTG TCGTTCAGGA   10500

TGACCATGGG GACCATGGGT CTGAGCCTGT GACCCTCCAG TCTACAGTGT GTTGGTGAGG   10560

AAGGAGCAGT TGTCACTGGG GTCACTGGCA ATGGGCATGC CTCCATCTAG CTTAGGCAAG   10620

ATGCTTAGAC TCAGAGCCAG AGAGTGAAAC CCAGACACTA ATGAGCTGTC GGTGTTGGTG   10680

TGTGTTCTCT TCCTCTTCCA GTGGAACATG ACAAGGAATT CTTCCACCCA CGCTACCACC   10740

ATCGAGAGTT CCGGTTTGAT CTTTCCAAGA TCCCAGAAGG GGAAGCTGTC ACGGCAGCCG   10800

AATTCCGGAT CTACAAGGAC TACATCCGGG AACGCTTCGA CAATGAGACG TTCCGGATCA   10860

GCGTTTATCA GGTGCTCCAG GAGCACTTGG GCAGGTGGGT GCTATACGGG TATCTGGGAG   10920

AGGTGCTGAG TTTCCTCTGG GGGCAGAGGA AGAAGGTGGT GAGGGTTTCC CTCCCCTCCC   10980

ACCCCATGAG CTCTGCTTCC CATCTGTTGG GGTAGTGGAG CTGTGACCTG CTAACGCGAA   11040

GCCCGTGTCT CTCCTCCTCT CTCGCAGGGA ATCGGATCTC TTCCTGCTCG ACAGCCGTAC   11100

CTCTGGGCCT CGGAGGAGGG CTGGCTGGTG TTTGACATCA CAGCCACCAG CAACCACTGG   11160

GTGGTCAATC CGCGGCACAA CCTGGGCCTG CAGCTCTCGG TGGAGACGCT GGATGGTGAG   11220

TCCCCCGCCA CTGCCAGTCC TAATGCAGCC TGTGCTCCTG GACTTCAGGA GGGTCTCAGC   11280

AGTGCTCATG CTTGCTTCAC TACAAACAGG CTTCCCCGCC CCTCCCAACC AGTACTCCAT   11340

GTTCAGCCTT TTGATCCTGC AGCCCTGTCC CGCTCGTGGC CCTCCTGTAA CTGCTCTTCT   11400

GTGCACTTGG CTGCTTCCTG TCCAGGGCAG ACGATCAACC CCAAGTTGGC GGGCCTGATT   11460

GGGCGGCACG GGCCCCAGAA CAAGCAGCCC TTCATGGTGG CTTTCTTCAA GGCCACGGAG   11520

GTCCACTTCC GCAGCATCCG GTCCACGGGG AGCAAACAGC GCAGCCAGAA CCGCTCCAAG   11580

ACGCCCAAGA ACCAGGAAGC CCTCGGATGG CCAACGTGGC AGGGTATCTT AGGTGGGAGG   11640

GATCACAGAC CCACCACAGG AACCCAGCAG GCCCCGGCGA CCGCAGGAGA CTGACTAAAA   11700

TCATTCAGTG CTCACCAAGA TGCTCTGAGC TCTCTTCGAT TTTAGCAAAC CAGGAGTCCG   11760

AAGATCTAAG GAGAGCTGGG GGTTTGACTC CGAGAGCTCG AGCAGTCCCC AAGACCTGGT   11820
```

```
CTTGACTCAC GAGTTAGACT CCACTCAGAG GCTGACTGTC TCCAGGGTCT ACACCTCTAA    11880

GGGCGACACT GGGCTCAAGC AGACTGCCGT TTTCTATATG GGATGAGCCT TCACAGGGCA    11940

GCCAGTTGGG ATGGGTTGAG GTTTGGCTGT AGACATCAGA AACCCAAGTC AAATGCGCTT    12000

CAACCAGTAG AAAATTCACC AGCCCGCAGA GCTAAGGTTG GGTGGACATT AGGGTTGGTT    12060

GATCCAGGAG CTCAACAGTG TCCTCTGAGC CCCAGCTCCT TCTGCCCCAC CCCACCATCT    12120

TCAGTGCTGC TTCCTCTCAA GGCCACAGCT GTAGTTGGCC AGGGGGCTT CATTATTTTT     12180

TGCTCCTGGG CAGTAGGAGG AAGAGAATGA ATGTCTCTCC ATGGGTCTTT CTTAGGAATG    12240

TGGGAACTTT TTCCAGAAGT CTCTATGTCT TTTAGTTTGT GTTGGGTCAC TTGCCCTTCC    12300

TGAACCACTT CCTGACTCCT GGACAGGATG TGCACTGATG AGCTTAGCTT TGGGGATCTA    12360

ATAGTGACTT TACAAAGCCT CTTTGAGAAG GTGACATTGG AACCAAGGCT TGAGCAGACA    12420

CAACAAAGAT TGCAGGGAGG GGCATTGCAG GTGGAGGAAA CGGCACATGC AAGAGCCCTG    12480

CGTGGGAGTG AGCTTGGTGT TTGGTCAATC AGTTGTCAGA GCACACCGGG CCCTGTCAGC    12540

AGGCACAGCC TGGGCCTGCT CTGAGTATGA CAGAGAGCCC CTGGGAAGTT GTAGGTGGAG    12600

GAAAGACAGG TCATGACTAG GAAAAAAGCA ATCCCTCTGT TGTGGGGTGG AAGGAAGGTT    12660

GCAGTGTGTG TGAGAGAGAG ACAAGACAGA CAGACAGACA CTTCTCAATG TTTACAAGTG    12720

CTCAGGCCCT GACCCGAATG CTTCCAAATT TACGTAGTTC TGGAAAACCC CCTGTATCAT    12780

TTTCACTACT CAAAGAAACC TCGGGAGTGT TTTCTTCTGA AAGGTCATCA GGTTTTGACT    12840

CTCTGCTGTC TCATTTCTTC TTGCTGGTGG TGGTGATGGT TGCTTGTCCC AGGCCCTGTC    12900

CCGCATCCTC TTGCCCCTGC AGAGGGATGA GTGTGTTGGG GCCTCACGAG TTGAGGTTGT    12960

TCATAAGCAG ATCTCTTTGA GCAGGGCGCC TGCAGTGGCC TTGTGTGAGG CTGGAGGGGT    13020

TTCGATTCCC TTATGGAATC CAGGCAGATG TAGCATTTAA ACAACACACG TGTATAAAAG    13080

AAACCAGTGT CCGCAGAAGG TTCCAGAAAG TATTATGGGA TAAGACTACA TGAGAGAGGA    13140

ATGGGGCATT GGCACCTCCC TTAGTAGGGC CTTTGCTGGG GGTAGAAATG AGTTTTAAGG    13200

CAGGTTAGAC CCTCGAACTG GCTTTTGAAT CGGGAAATTT ACCCCCCAGC CGTTCTGTGC    13260

TTCATTGCTG TTCACATCAC TGCCTAAGAT GGAGGAACTT TGATGTGTGT GTGTTTCTTT    13320

CTCCTCACTG GGCTCTGCTT CTTCACTTCC TTGTCAATGC AGAGAACAGC AGCAGGCACC    13380

AGAGGCAGGC CTTGTAAGAA GCACGAGCTG TATGTCAGCT TCCGAGACCT GGGCTGGCAG    13440

GTAAGGGGCT GGCTGGGTCT GTCTTGGGTG TGGGCCCTCT GGCGTGGGCT CCCACAGGCA    13500

GCGGGTGCTG TGCTCAGTCT TGTTTCTCAT CTCTGCCAGT TAAGACTCCA GTATCAAGTG    13560

GCCTCGCTAG GGAAGGGGAC TTGGGCTAAG GATACAGGGA GGCCTCATGA AATCCGAGAG    13620

CAGAAATGTG GTTGAGACTT GAACTCGAAC CAGGAACCCA AACACTTTGG ACTCTGAACC    13680

CCATTCTCTG CATGCACCTC ATTCCCATCC CTTGGCTGGC TGCTTCTCAA GATGATGCCG    13740

GGCCGTGTGT TTGAATGTAG ATACCTGGGG AGCCATCTCC CCCTCTGCCC TCTGACTTCA    13800

TTTACCCCAT TCCCATTCCC ACGGGAGGGA CGGATCTCCC CAGCTTGGTT CAGGCGCTTG    13860

TTCCTGAACC AGTCAACTGT TTCAGGGGTG GGGTCATGTT ACTGGCACAT GGCTGCCCCC    13920

TCTGGAGCCA TTTGCATGGA GTGAGGCAAA AGGCAGGGGA TGAATCTAGG AGAGGAGTGA    13980

GGGTCATGTG ATCCACCTGC CGTGAGCTCT GGATCGTGAT TCTCATTCAG CAGTCACGAG    14040

CATCTCGAGC GTTCTGGGCC CTGTTCTAGG TACTGGATTG GAGATGCAGC GATGAACACT    14100

GCAATGTGTC TGCCCTGTGG GGCTCAAATA TCCCTGAGA GGGTATTGTC ATGAGGTCAT      14160

CAGGGCAACT GGTGGTATTC TACCCTCAGG GAGCTTGTAG TTCAGTGGGA GAGTCCAGAA    14220
```

```
TCTTCCCTGG GGATTATGCC CAGACACACT CAGGGCGTAC GTGCACACAG CCAGCTCTGA   14280

GCCCTCCTGT GAGCCTGCCC TCAGGACTGA TGACCACATC TACCTGCAGC TGGGACAGAA   14340

CCCAAACTCC AGGGGCCTCT GCTGGAAGAT TCCATGTGCT TAAGCATCAC TGAGGAGTAT   14400

ATTGATTATT GGGCAACATT TCTGTGCCAC CCAGACCCTA GAGGCAAGGA TGGCACATGG   14460

ATCCCTTACT GACCAGTGCA CCCGGAGCCA GCATGGGTGA TGCCATTATG AGTTATTAGC   14520

CTCTCTGGCA GGTGGGCAAA CCGAGGCATG GAGGTTTGTT TAAGGTGAAC TGCCAGTGTG   14580

TGACCACCTA GTGGGGTAG AGCTGATGAT TGCCTCACAC CGGAGGCTCC TTCCTGTGCC   14640

GCGTTCTGTC CAGAAGACAC AGCCATGGAT GTCCATTTTA GGATCAGCCA AGCCCGTGGG   14700

GCTTTCCTTC ATTTTTATTT TATGTTTTTT TAGAAATGGG GTCTTGCTCT GTCACCCAGG   14760

CTGGGGTGCA GTGGTGTGAT CATACGTCAC CGCAGCTTTG AGCCGTCTTC CCACTCAGTC   14820

TACTAAGCTT GGACTATAGG CCAAGACTAT AGAGTGGTCC TTCTTTCCAT TCTTTTGGGA   14880

CCATGAGAGG CCACCCATGT TTCCTGCCCC TGCTGGGCCC TGCTGCTCAG AAGGCATGGT   14940

CTGAGGCTTT CACCTTGGTC GTGAGCCTTC GTGGTGGTTT CTTTCAGCAT GGGGTTGGGA   15000

TGCTGTGCTC AGGCTTCTGC ATGGTTTCCC ACACTCTCTT CTCCTCCTCA GGACTGGATC   15060

ATCGCGCCTG AAGGCTACGC GCGCTACTAC TGTGAGGGGG AGTGTGCCTT CCCTCTGAAC   15120

TCCTACATGA ACGCCACCAA CCACGCCATC GTGCAGACGC TGGTGGGTGT CACGCCATCT   15180

TGGGGTGTGG TCACCTGGGC CGGGCAGGCT GCGGGGCCAC CAGATCCTGC TGCCTCCAAG   15240

CTGGGGCCTG AGTAGATGTC AGCCCATTGC CATGTCATGA CTTTTGGGGG CCCCTTGCGC   15300

CGTTAAAAAA AAATCAAAAA TTGTACTTTA TGACTGGTTT GGTATAAAGA GGAGTATAAT   15360

CTTCGACCCT GGAGTTCATT TATTTCTCCT AATTTTTAAA GTAACTAAAA GTTGTATGGG   15420

CTCCTTTGAG GATGCTTGTA GTATTGTGGG TGCTGGTTAC GGTGCCTAAG AGCACTGGGC   15480

CCCTGCTTCA TTTTCCAGTA GAGGAAACAG GTAAACAGAT GAGAAATTTC AGTGAGGGGC   15540

ACAGTGATCA GAAGCGGGCC AGCAGGATAA TGGGATGGAG AGATGAGTGG GGACCCATGG   15600

GCCATTTCAA GTTAAATTTC AGTCGGGTCA CCAGGAAGAT TCCATGTGAT AATGAGATTA   15660

ACGTGCCCAG TCACGGCGAC ACTCAGTAGG TGTTATTCCT GCTCTGCCAA CAGCAACCAT   15720

AGTTGATAAG AGCTGTTAGG GATTTTGTCC TTTTGCTTAG AATCCAAGGT TCAAGGACCT   15780

TGGTTATGTA GCTCCCTGTC ATGAACATCA TCTGAGCCTT TCCTGCCTAC TGATCATCCA   15840

CCCTGCCTTG AATGCTTCTA GTGACAGAGA GCTCACTACC AGGACTACTC CCTCCTTTCA   15900

TTTAGTAATC TGCCTCCTTC TTTTCTTGTC CCTGTCCTGT GTGTTAAGTC CTGGAGAAAA   15960

ATCTCATCTA TCCCTTTCAT TTGATTCTGC TCTTTGAGGG CAGGGGTTTT TGTTTCTTTG   16020

TTTGTTTTTT TAAGTGTTGG TTTTCCAAAG CCCTTGCTCC CCTCCTCAAT TGAAACTTCA   16080

AAGCCCTCAT TGGGATTGAA GGTCCTTAGG CTGGAAACAG AAGAGTCCTC CCCAACCTGT   16140

TCCCTGGCCT GGATGTGCTG TGCTGTGCCA GTATCCCCTG GAAGGTGCCA GGCATGTCTC   16200

CCCGGCTGCC AGGGGACACA TCTCTATCCT TCTCCAACCC CTGCCTTCAT GGCCCATGGA   16260

ACAGGAGTGC CATCGCCCTG TGTGCACCTA CTTCCATCAG TATTTCACCA GAGATCTGCA   16320

GGATCAAAGT GAATTCTCCA GGGATTGTGA AATGATGCGA TTGTGGTCAT GTTTAAAAGG   16380

GGGCAACTGT CTTCTAGAGA GTCCTGATGA AATGCTTCCA GAGGAAATGA GCTGATGGCT   16440

GGAATTTGCT TTAAAATCAT TCAAGGTGGA GCAGGTGGGG AAGGGTATGG ATGTGTAAGA   16500

GTTTGAAATT GTCCATCATA AAATGTGTAA AAAGCATGCT GGCCTATGTC AGCAGTCACA   16560

GCCTGGAGGT GGTAACAGAG TGCCAGTCAC TGATGCTCAA GCCTGGCACC TACAGTTGCT   16620
```

```
GGAAACCCAG AAGTTTCACG TTGAAAACAA CAGGACAGTG GAATCTCTGG CCCTGTCTTG    16680

AACACGTGGC AGATCTGCTA ACACTGATCT TGGTTGGCTG CCGTCAGCTT AGGTTGAGTG    16740

GCGGTCTTCC CTTAGTTTGC TTAGTCCCCG CTATTCCCTA TTGTCTTACC TCGGTCTATT    16800

TTGCTTATCA GTGGACCTCA CGAGGCACTC ATAGGCATTT GAGTCTATGT GTCCCTGTCC    16860

CACATCCTCT GTAAGGTGCA GAGAAGTCCA TGAGCAAGAT GGAGCACTTC TAGTGGGTCC    16920

AAGTCAGGGA CACTATTCAG CAATCTACAG TGCACAGGGC AGTTCCCCAA CAGAGAATTA    16980

CCTGGTCCTG AATGTCGGAT CTGGCCCCTT CCTTCCCCAC TGTATAATGT GAAAACCTCT    17040

ATGCTTTGTT CCCCTTGTCT GCAAAACAGG GATAATCCCA GAACTGAGTT GTCCATGTAA    17100

AGTGCTTAGA ACAGGGAGTG CTTGGCTTGG GGAGTGTCAC CTGCAGTCAT TCATTATGCC    17160

CAGACAGGAT GTTTCTTTAT AGAAACGTGG AGGCCAGTTA GAACGACTCA CCGCTTCTCA    17220

CCACTGCCCA TGTTTTGGTG TGTGTTTCAG GTCCACTTCA TCAACCCGGA AACGGTGCCC    17280

AAGCCCTGCT GTGCGCCCAC GCAGCTCAAT GCCATCTCCG TCCTCTACTT CGATGACAGC    17340

TCCAACGTCA TCCTGAAGAA ATACAGAAAC ATGGTGGTCC GGGCCTGTGG CTGCCACTAG    17400

CTCCTCCGAG AATTC                                                     17415

(2) INFORMATION FOR SEQ ID NO:2:

(i) SEQUENCE CHARACTERISTICS:
        (A) LENGTH: 2300 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2300
        (D) OTHER INFORMATION: /note= "MOP1 UPSTREAM SEQUENCE"

(xi) SEQUENCE DESCRIPTION: SEQ ID NO:2:

TGCATAGGTC ACACATCCCT CCTCTACCCA AGGCTAGCCA GGTGCCCTAT CTCTCCCTTC      60

TTCGGTGCCT CCTCCGACTG GGCTCTGACG TTCTCAGAGA GAACGAAAGG GAAAGACTGC     120

TTGCTACCCT TCTGTTCCGG ACCTTACTGA AGGGCCTTAG TGTTTCCAGG GGCCCAAGAA     180

CCAGGTAGCC GTGGAGGTTG CCATGCTTGC CTGCCCACTC ACCCAACGTT CTCCTGCCTG     240

GCCTGTGTGT GGCACCCATG CAGGCCACAG AAGGCCACAC ACAGCCTTCA GGATGAGGCA     300

GGGCCCCTTT GTTTATTCAA TATCAAGAAC TGTAACGTGG TCACCGGAGG TCATGTCTCC     360

AGCTCGCAGC CTGCTTGGCC TCAGATCACC CACCACAGCA GGTCCAGGGA GGGGCCTCTC     420

AGGTCTGCAC TGGGCCAGGG ACTCAGTACT GGTGGGCATC CAAGGCCTGG GCTAAGACCT     480

GCAAGTTTCT TTTAGCCCCT CAGACAGTCA CATCACCTAA AATTCCTACC AAGGAGCCCT     540

GAGAGACCTA GGTAGTTATC TCTGTTCCAG GAAGCCTGAA AGACCAGGCT TCCCATCTCA     600

CCCTAGGACT TCAAGAGGGA CCCCCTACTC AAGGCCCTTC CCCAGCCCCT ACTTGCCATT     660

TTACCACCCC TGAAACGCTT GCTTGTCGCC CACCTTCAGC AAAGCAGGAA GCCTGGCTCA     720

CCATCCCCAC TCACTCACTG CCATTCTGGG TGAAGGCTGC TTTGCTCCCA TTTTTCAGAT     780

TAGGAAACGG AGGCTCCAAA GAGCAGCAAT CCACTGAGAG ACCCAGTATC TGTCTGGGAC     840

GTTTCCTCCT GGGAGGAGAG GGAGGCTAGT CCTTTGAGAC AGGAAAATCG AGTCGGGAGC     900

TCTTCTGAAC TTGGGTACCA ACTGCCTACT CCTCAGGCCC CTGACCTGGG GCTAGGGGTA     960

GGGGTTATTA GACAGTGAGG TACCAAAGGA CTCATGTCAG GACCCCGCCC CCCCAAGAGA    1020
```

-continued

```
GGAGGGGGTG GGAACATTCT CTAGTCCCAG ATTTCACTTA TGTACTCTGT AGAGCTGCAG      1080

CATCTGGGGT TTGAAGGCTT TGGGTTAAAA GATACTTGGG AAGGAAAAGC CGAGAAGTAC      1140

CTGGGCCCGG ATCCCTTGGG TGCTGGACTT GAGGGGAGGT GTGTGTGTGT GTGTGTGTGA      1200

GTGTGTGTGT ATGTATGTGT GTGTTGGGGG AGTGAAGTGT AGAAAGAACT TTATCTCCAC      1260

ATTATCTCTG CCCGTCCTGG AAGGTTCCCA GAGGAAGTGG CACCCGAGGG GGGAGGGGCA      1320

GGGAGAACGT TCCCCGAGGA ACAAAAGCCA GGATAGCAGA GGGGCAAGCG GTGGGGGTAC      1380

CGAGGGGGTT TTGCATGACT GGAGCAAATG GAGTGTTGGG GGGGCGGTT CGAAAGATGA       1440

GCCAGGTCCA AGAGTGGCCA CCTCCGAGGA GCCTTCTCGG ATTCCTGCGC TCCCTCCTGG      1500

ATGCTTTCCT AGCACAGCCC TTAGTTGCTA CACTTTGGCC ACTTCCAAGT GCGAGTCCCG      1560

AGAGAGCTGG GCAGATTGGG ATTCTTCTCT CTGGGTCCCT GCGGCGTCTG TCCCAGTGCC     1620

GGACACCCGG TGGGCACTCG GTAAATATTT GTAGAGCGCC CTGGGAGGAA TGAATGAAGC     1680

CATTGGGCCA GGCTTGGGGA GGGCGGGGAC AGGCGCAGGT GGGAGGCAGC GGGAGCGGGA      1740

GGGGCGGGGA AGTCAGTCCT CCCGCTCCTC CCCCGCTCCC CGGCCCCAGC GCGCCCAACT     1800

CCGGGGCTCC CGAGGCGGCG GGCGGGCGAT CCGGGCGCGC AGGGCCCTTG TATTGGGCAC      1860

GCGGGAGATC GGAAAGGGGT TTGTTGCTGG TGCCCGCGGG CCTGAGCGCG ATCAGAGCGG      1920

GAGGAGGGAG CTAGGGTTCG CTCAGCGCCC AGCTGCCTCT CCGGCACTCG CTCTCCGGAC     1980

TTGTAGGTCT GCAAGCTGCT GCTCCTCCCA CCCCGGCCCG CCTCCTCGCT CTCTTGCTCG      2040

CTCTCTGGAG TTGCTGTGCT AGCCTTGCCG TGCGTCCTGG CGAGTGCGGG CCGAGGGGCC      2100

CCGGGCCAGA ACTGAGTAAA GGACAGGGGC GTCCCGGGCA AAGCGCAGCC GGCCGGGGAG     2160

TGGCCATGTG TGGCGAGGCC GCCTTGAAGC TCGCCTGCAG CAAGTGACCT CGGGTCGTGG      2220

ACCGCTGCCC TGCCCCCTCC GCTGCCACCT GGGGCGGCGC GGGCCCGGTG CCCCGGATCG      2280

CGCGTAGAGC CGGCGCGATG                                                 2300
```

(2) INFORMATION FOR SEQ ID NO:3:

(i) SEQUENCE CHARACTERISTICS:
        (A) LENGTH: 2997 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2997
        (D) OTHER INFORMATION: /note= "MOP1 TERMINAL SEQUENCE"

(xi) SEQUENCE DESCRIPTION: SEQ ID NO:3:

```
TAGCTCTTCC TGAGACCCTG ACCTTTGCGG GGCCACACCT TTCCAAATCT TCGATGTCTC        60

ACCATCTAAG TCTCTCACTG CCCACCTTGG CGAGGAGCCA ACAGACCAAC CTCTCCTGAG       120

CCTTCCCCTC ACCTCCCCAA CCGGAAGCAT GTAAGGGTTC CAGAAACCTG AGCGTGCAGG      180

CAGCTGATGA GCGCCCTTTC CTTCTGGCAC GTGACGGACA AGATCCTACC AGCTACCACA       240

GCAAACGCCT AAGAGCAGGA AAAATGTCTG CCAGGAAAGT GTCCATTGGC ACATGGCCC        300

CTGGCGCTCT GAGTCTTTGA GGAGTAATCG CAAGCCTCGT TCAGCTGCAG CAGAAGGAAG      360

GGCTTAGCCA GGGTGGGCGC TGGCGTCTGT GTTGAAGGAA AACCAAGCAG AAGCCACTGT      420

AATGATATGT CACAATAAAA CCCATGAATG AAAATGGTTA GGATACAGAT ATATTTTCCT      480

AAACAATTTA TCCCCGTTTC TTGGTTTATT CTGACTTTGT AAACAGAAAA GCCGGGGCTG      540
```

```
TGGAGGATGG AGAGGCCCCT CCTTTCCGTC TCGTCTCGTT GTGTGTGTTT ACCAGACCTG      600

CCCAAATCCA GCCTGTAGGG AGGAGGAGGA GGATGTCTGC TCAGAAGAGG CCAGTGAGGG      660

ATGTGGCCTC AAAGGGTGTT GGGATGAAGA TGGAGGGAGG TATGCATGCA CACACACACA      720

CACACACACA CACACACACA CATGCATGAT ACACACACAC ACACACACAC ACACACACGA      780

TGCACACACA CACACACACA CACACACACA CACACACGCA CGCACGCACG CACACGCACG      840

CATGCATGCA CACACACACG CACACACACA TCTGAAGCGC ATGTAGACTT TGGAATGGCT      900

CTGCCAGTCC CTCAGCCCCA ATTCCTGCCC CATGGTAGGA AATCCATGAG AAAAGCAAAG      960

CTAACAAGCA CAGCGGACCC TACCTGAGGA AGCACAGGGG ATGCAGGCTC TTCAGGACAC     1020

TGTCCTCCAA ACAAGGCCCC TCTGGCACCT CTGTGGCCGA GCTCCGGAGC CAGGTCCTGG     1080

CCTTCACAGC TGCCTCTCTT CACTCTCAAC CCTAACAGAA GGTTCTGCGA CAGATTGGTT     1140

TCTGGATCTG AGGGAGATGG CAGAACAGGG TTGTACTGGC TTAGAAGGTT CAACCATGCT     1200

TCCTGCTTCA GAGGTGGGAT GTTGGTTATG GCTCAAACAA GGCCTCTCTG CCTGAGTTTG     1260

CAGAGCCCCA GCTGCCCCAA TGGTTCCTAG CTTCAAATGC AGAGGGTTAA ACTGGCTGCC     1320

AGTGTTTCCT GCATCCACAC AAAGAATGAG GTTAGCCAGG CAGGACCTAT GGCCATGTCG     1380

CATCTGGTCA GGTGGGGAAC CAATTCTTCA TGTCTGTGTC CCTGGAAACA CTGGGCTCTC     1440

TTCTGTTCTG TTTTAGTTTT TCTTCTTCAG TAGCTTGGGC TGCAGCTTCT ACTCTGCCCA     1500

TTCGATGTGG GGGAAGGCCA TTTCTTTTTG TAATTTGTTC TGTGTGTTTG CAGATCTGGG     1560

GCTTTTTGTG TGACTCCCCT GTGGTGCACA TTTTACTTTA GAGCCCTAGT CTGCCTGCAG     1620

TCGGTGTCTC TTATACGTTT AAATGTGTAA ATAGTTGTGA CAAGACAAAG AAATTATTTA     1680

TTTCCATCTG AAGCTCTTTC CAAAGGCTCC TCACAGAGAA CAATGAGGCC GACTTCCTTC     1740

AGTCTGTTTG TTTTCTTATT TAAGACTATT TATTAACAGT TGGACCGATG TACCCATAGC     1800

TGTCGAATAA AGTGGTCCTT AGTGAAAATT CTGTATAAAT AGAGTAAGAA GGGGTTTGAC     1860

TTTGCAATAA AAGGAGACAT TTGGTTCTGG TTGTCCGACC CATGTGTGTA TTTGTGTCTT     1920

TCCCCCTGAA CTCCTGGACA CTGGAGTCTC ATCGGCTGAG AACCCTCGAC CTTGATCTCG     1980

ACTGTTAACG GGATGTTTAT CATCCAGGCC CAGGGGAAGT CGGGCGCTCC TCAATATTTG     2040

GTGCAGCTGT GTGGGGCTCC CTGGGCGGGA GAGACGGAAC CAAACAACAA ATGTGAGTTT     2100

GGTAAGGCTG GATGGCAAAG AGTGCCTTTG ATTGAACTAC AGCCCAGCTG TCAGCAGCTG     2160

CTTCAAAGAG GCAGGGGTA AATTAGCTGT GTTTACTGCT AACATAGTCG AAAGATTTAG      2220

TCATCCCAAT AAAATAGAGG CACAAGAGAG AAGAGGGGGG GGTGTATACC CCAAACTTGA     2280

AAGCCATGCT GGCCTCACAG CTGGCGTCAT TCAGTGCCCG TCACACCCGG GCAGTTGGGG     2340

GCTGCCCTCG CAGGCCAAGC TGTGGAGGTG GGCAGCCCAC CGCAGGCTGG AGAAGGGAGT     2400

GCCCCCCACC TCCCCGGCAA GCTCAGGGCA GTGCTCATCT GGCTACATCG GTCTTTGAAG     2460

TGCGCACGAA GGTCACCTGA CGGATGTTTC TAGAATCCCA GGCGATGCTT GGGACAGGCT     2520

GCTCTCTCTT CCCCTGTTGA CTCAGACCCA GCAACCCAGC CGTCCTAACA CATTCCAGCC     2580

CCTGCGATTT CTAAACCTTT CCTGTCACTG TCCCGACAAC TCAGCTTTTG TTCTGTTTTC     2640

CAGGCTGAAG CCCAGAGCCA CAAGCCGGAG GGTCCAGATG TGGCCTCTCA GATGTGTGCC     2700

TTAGCCTCTC AACCCCACCC CCACCCCCAA CCCCAGTGAT GTTTACACAT CTTAAAAAAC     2760

ACTAATCTGT TGCCAATATG TTTTTGCAAA TAAGGAGTTT GGGCTTCTCT TGAGCGGGCC     2820

ACCTGGTTCC TCCCTGTGTG CTGCTCCTAA CTGAACAGAG GTGCCAGGGC CGTTGTCACA     2880
```

```
CATACACACA CCCCCGCCAT GGCCTCATCC ACAAACGGTC GAGGTCAGCT GACATCTTCA      2940

AAATGGCTGA CGGATGTCTA CTTGTGCCCA CGACCCAAAA GGAATAGGAA AATGGAA         2997
```

(2) INFORMATION FOR SEQ ID NO:4:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..9
        (D) OTHER INFORMATION: /note= "WT1/EGR CONSENSUS SEQUENCE"

(xi) SEQUENCE DESCRIPTION: SEQ ID NO:4:

```
GNGNGGGNG                                                             9
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /note= "WT1/EGR HUMAN TCC BINDING
            SITE"

(xi) SEQUENCE DESCRIPTION: SEQ ID NO:5:

```
TCCTCCTCCT CCTCCTCCTC C                                               21
```

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..15
        (D) OTHER INFORMATION: /note= "WT1/EGR MOUSE TCC BINDING
            SITE"

(xi) SEQUENCE DESCRIPTION: SEQ ID NO:6:

```
TCCTCCCGCT CCTCC                                                      15
```

(2) INFORMATION FOR SEQ ID NO:7:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

-continued (ix) FEATURE:
    (A) NAME/KEY: misc_feature
    (B) LOCATION: 1..9
    (D) OTHER INFORMATION: /note= "HUMAN FTZ BINDING SITE"

(xi) SEQUENCE DESCRIPTION: SEQ ID NO:7:

TCAAGGTCA                                                              9